United States Patent
Foley et al.

(10) Patent No.: US 10,426,918 B2
(45) Date of Patent: Oct. 1, 2019

(54) FLUSHABLE CATHETERS

(71) Applicant: Hollister Incorporated, Libertyville, IL (US)

(72) Inventors: Adam J. Foley, Swords (IE); John T. Clarke, Galway (IE)

(73) Assignee: Hollister Incorporated, Libertyville, IL (US)

( * ) Notice: Subject to any disclaimer, the term of this patent is extended or adjusted under 35 U.S.C. 154(b) by 564 days.

(21) Appl. No.: 15/021,767

(22) PCT Filed: Dec. 10, 2014

(86) PCT No.: PCT/US2014/069508
§ 371 (c)(1),
(2) Date: Mar. 14, 2016

(87) PCT Pub. No.: WO2015/089165
PCT Pub. Date: Jun. 18, 2015

(65) Prior Publication Data
US 2016/0228679 A1    Aug. 11, 2016

Related U.S. Application Data

(60) Provisional application No. 62/011,078, filed on Jun. 12, 2014, provisional application No. 61/915,220, (Continued)

(51) Int. Cl.
*A61M 25/00* (2006.01)
*A61L 29/14* (2006.01)
(Continued)

(52) U.S. Cl.
CPC ......... *A61M 25/0017* (2013.01); *A61L 29/14* (2013.01); *A61M 25/0043* (2013.01); (Continued)

(58) Field of Classification Search
CPC ............ A61M 27/008; A61M 25/0017; A61M 25/0043; A61M 25/008; A61L 29/14
See application file for complete search history.

(56) References Cited

U.S. PATENT DOCUMENTS

| 3,583,391 A | 6/1971 | Cox et al. |
| 3,621,848 A | 11/1971 | Magovern |

(Continued)

FOREIGN PATENT DOCUMENTS

| CN | 2240371 | 11/1996 |
| CN | 101300036 A | 11/2008 |

(Continued)

OTHER PUBLICATIONS

Rachna N. Dave, Hiren M. Joshi, and Vayalam P. Benugopalan, Novel Biocatalytic Polymer-Based Antimicrobial Coatings as Potential Ureteral Biomaterial, Feb. 1, 2011, 44(2): 845-853.

(Continued)

*Primary Examiner* — Adam Marcetich
*Assistant Examiner* — Jessica R Arble
(74) *Attorney, Agent, or Firm* — Cook Alex Ltd.

(57) ABSTRACT

A flushable catheter assembly includes a catheter shaft having proximal and distal end portions. The catheter may include a funnel assembly associated with the distal end portion of the catheter shaft and/or an introducer cap assembly associated with the proximal end portion of the catheter shaft. A groove is defined along at least a portion of an outer perimeter of the funnel assembly or introducer cap assembly, with the groove being configured to receive at least a portion of the catheter shaft for wrapping the catheter shaft around the outer perimeter when disposing of the catheter. Instead of (or in addition to) a groove, one or more channels may pass through the funnel assembly to receive a portion of the catheter shaft for securing the catheter shaft to the funnel (Continued)

assembly for disposal. The catheter assembly and/or its individual components may be formed of a water disintegrable material.

20 Claims, 11 Drawing Sheets

Related U.S. Application Data filed on Dec. 12, 2013, provisional application No. 61/915,396, filed on Dec. 12, 2013.

(51) Int. Cl.
*A61L 29/04* (2006.01)
*A61L 29/06* (2006.01)

(52) U.S. Cl.
CPC ........... *A61L 29/041* (2013.01); *A61L 29/043* (2013.01); *A61L 29/06* (2013.01); *A61M 25/0082* (2013.01); *A61M 25/0097* (2013.01); *A61M 2205/02* (2013.01)

(56) References Cited

U.S. PATENT DOCUMENTS

| | | |
|---|---|---|
| 3,702,610 A | 11/1972 | Sheppard et al. |
| 3,861,396 A | 1/1975 | Vaillancourt et al. |
| 3,894,540 A | 7/1975 | Bonner, Jr. |
| 4,062,363 A | 12/1977 | Bonner, Jr. |
| 4,100,309 A | 7/1978 | Micklus et al. |
| 4,227,533 A | 10/1980 | Godfrey |
| 4,413,986 A | 11/1983 | Jacobs |
| 4,465,481 A | 8/1984 | Blake |
| 4,610,671 A | 9/1986 | Luther |
| 4,668,221 A | 5/1987 | Luther |
| 4,762,738 A | 8/1988 | Keyes et al. |
| 4,769,005 A | 9/1988 | Ginsburg et al. |
| 4,772,279 A | 9/1988 | Brooks et al. |
| 4,790,817 A | 12/1988 | Luther |
| 4,790,831 A | 12/1988 | Skribiski |
| 4,795,439 A | 1/1989 | Guest |
| 4,840,622 A | 6/1989 | Hardy |
| 4,883,699 A | 11/1989 | Aniuk et al. |
| 4,906,238 A | 3/1990 | Greenfeld et al. |
| 4,952,359 A | 8/1990 | Wells |
| 4,954,129 A | 9/1990 | Giuliani et al. |
| 4,994,047 A | 2/1991 | Walker et al. |
| 5,002,526 A | 3/1991 | Herring |
| 5,009,648 A | 4/1991 | Aronoff et al. |
| 5,089,535 A | 2/1992 | Malwitz et al. |
| 5,098,535 A | 3/1992 | Nakakoshi et al. |
| 5,102,401 A | 4/1992 | Lambert et al. |
| 5,195,962 A | 3/1993 | Martin et al. |
| 5,270,086 A | 12/1993 | Hamlin |
| 5,332,524 A * | 7/1994 | Kaylor .................. C08J 3/05 |
| | | 252/363.5 |
| 5,344,011 A * | 9/1994 | DiBernardo ........ A61M 25/002 |
| | | 206/364 |
| 5,439,454 A | 8/1995 | Lo et al. |
| 5,468,526 A | 11/1995 | Allen et al. |
| 5,472,417 A | 12/1995 | Martin et al. |
| 5,569,219 A | 10/1996 | Hakki et al. |
| 5,601,538 A | 2/1997 | Deem |
| 5,616,126 A | 4/1997 | Malekmehr et al. |
| 5,688,459 A | 11/1997 | Mao et al. |
| 5,776,611 A | 7/1998 | Elton et al. |
| 5,792,114 A | 8/1998 | Fiore |
| 5,800,412 A | 9/1998 | Zhang et al. |
| 5,804,653 A | 9/1998 | Weng |
| 5,904,703 A | 5/1999 | Gilson |
| 5,985,394 A | 11/1999 | Mao et al. |
| 6,017,334 A | 1/2000 | Rawls |
| 6,030,369 A | 2/2000 | Engelson et al. |
| 6,063,063 A * | 5/2000 | Harboe ................. A61F 2/0009 |
| | | 604/256 |
| 6,066,120 A | 5/2000 | Whiteside |
| 6,071,618 A | 6/2000 | Cook, Jr. et al. |
| 6,090,075 A | 7/2000 | House |
| 6,213,990 B1 | 4/2001 | Roempke |
| 6,217,569 B1 | 4/2001 | Fiore |
| 6,447,835 B1 | 9/2002 | Wang et al. |
| 6,468,245 B2 | 10/2002 | Alexandersen |
| 6,471,684 B2 | 10/2002 | Dulak et al. |
| 6,488,659 B1 | 12/2002 | Rosenman |
| 6,585,721 B2 | 7/2003 | Fiore |
| 6,627,586 B1 | 9/2003 | Brooks et al. |
| 6,656,146 B1 | 12/2003 | Clayman et al. |
| 6,664,333 B2 | 12/2003 | Wang et al. |
| 6,713,140 B2 | 3/2004 | McCormack et al. |
| 6,726,654 B2 | 4/2004 | Rosenman |
| 6,942,635 B2 | 9/2005 | Rosenblatt et al. |
| 6,960,224 B2 | 11/2005 | Marino et al. |
| 6,976,973 B1 | 12/2005 | Ruddell et al. |
| 7,037,295 B2 | 5/2006 | Tiernan et al. |
| 7,128,862 B2 | 10/2006 | Wang |
| 7,156,824 B2 | 1/2007 | Rosenman |
| 7,182,906 B2 | 2/2007 | Chen |
| 7,402,620 B2 | 7/2008 | McGhee |
| 7,553,923 B2 | 6/2009 | Williams |
| 7,601,158 B2 | 10/2009 | Ouse |
| 7,641,757 B2 | 1/2010 | Kampa et al. |
| 7,662,146 B2 | 2/2010 | House |
| 7,731,740 B2 | 6/2010 | LaFont et al. |
| 7,789,873 B2 | 9/2010 | Kubalak et al. |
| 7,815,628 B2 | 10/2010 | Devens, Jr. |
| 7,820,284 B2 | 10/2010 | Terry |
| 7,824,517 B2 | 11/2010 | Kampa et al. |
| 7,833,280 B2 | 11/2010 | Stack et al. |
| 7,947,031 B2 | 5/2011 | DiMatteo et al. |
| 8,143,368 B2 | 3/2012 | Domb et al. |
| 8,168,249 B2 | 5/2012 | Utas et al. |
| 8,187,254 B2 | 5/2012 | Hissink |
| 8,388,583 B2 | 3/2013 | Stout |
| 8,388,585 B2 | 3/2013 | Tomes |
| 8,469,928 B2 | 6/2013 | Stout |
| 8,518,019 B2 | 8/2013 | Green |
| 8,569,402 B2 | 10/2013 | Henderson et al. |
| 2002/0016574 A1 | 2/2002 | Wang et al. |
| 2003/0165647 A1 | 9/2003 | Kaneko et al. |
| 2003/0187368 A1 | 10/2003 | Sata et al. |
| 2003/0228434 A1 | 12/2003 | Bailey et al. |
| 2004/0122382 A1 | 6/2004 | Johnson et al. |
| 2004/0210180 A1 | 10/2004 | Altman |
| 2004/0023258 A1 | 11/2004 | Kawabata et al. |
| 2004/0220550 A1 | 11/2004 | Schryver |
| 2004/0230177 A1 | 11/2004 | DiMatteo et al. |
| 2005/0049577 A1 | 3/2005 | Snell et al. |
| 2005/0109648 A1 | 5/2005 | Kerzman et al. |
| 2005/0131386 A1 | 6/2005 | Freeman et al. |
| 2005/0163844 A1 | 7/2005 | Ashton |
| 2005/0197627 A1 | 9/2005 | Huang et al. |
| 2005/0218154 A1 | 10/2005 | Selsby |
| 2005/0277862 A1 | 12/2005 | Anand |
| 2005/0283111 A1 | 12/2005 | Maurice |
| 2006/0173422 A1 | 8/2006 | Reydel et al. |
| 2006/0240064 A9 | 10/2006 | Hunter et al. |
| 2007/0043333 A1 | 2/2007 | Kampa et al. |
| 2007/0078412 A1 | 4/2007 | McGuckin, Jr. et al. |
| 2007/0088330 A1 | 4/2007 | House |
| 2007/0203502 A1 | 8/2007 | Makker et al. |
| 2007/0225649 A1 | 9/2007 | House |
| 2008/0015527 A1 | 1/2008 | House |
| 2008/0091145 A1 | 4/2008 | House |
| 2008/0097411 A1 | 4/2008 | House |
| 2008/0118544 A1 | 5/2008 | Wang |
| 2008/0147049 A1 | 6/2008 | House et al. |
| 2008/0171991 A1 | 7/2008 | Kourakis |
| 2008/0171998 A1 | 7/2008 | House |
| 2008/0172042 A1 | 7/2008 | House |
| 2008/0183262 A1 | 7/2008 | Dowling |
| 2008/0255510 A1 | 10/2008 | Wang |
| 2008/0268193 A1 | 10/2008 | Cherry et al. |
| 2008/0292776 A1 | 11/2008 | Dias et al. |
| 2008/0312550 A1 | 12/2008 | Nishtala |

(56) References Cited

U.S. PATENT DOCUMENTS

| | | |
|---|---|---|
| 2009/0018530 A1 | 1/2009 | Nielsen et al. |
| 2009/0036874 A1 | 2/2009 | Horowitz et al. |
| 2009/0234294 A1* | 9/2009 | Harvey ............. A61M 25/04 604/174 |
| 2009/0250370 A1 | 10/2009 | Whitchurch |
| 2009/0264869 A1 | 10/2009 | Schmid et al. |
| 2010/0030197 A1 | 2/2010 | House |
| 2010/0049146 A1 | 2/2010 | Nielsen et al. |
| 2010/0098746 A1 | 4/2010 | King |
| 2010/0100116 A1 | 4/2010 | Brister et al. |
| 2010/0137743 A1 | 6/2010 | Nishtala |
| 2010/0145315 A1 | 6/2010 | House |
| 2010/0198195 A1 | 8/2010 | Nishtala et al. |
| 2010/0204682 A1 | 8/2010 | Tanghoj et al. |
| 2010/0209472 A1 | 8/2010 | Wang |
| 2010/0215708 A1 | 8/2010 | Zumbuehl et al. |
| 2010/0312255 A1 | 12/2010 | Satake et al. |
| 2010/0323189 A1 | 12/2010 | Illsley et al. |
| 2011/0049146 A1 | 3/2011 | Illsley et al. |
| 2011/0071507 A1* | 3/2011 | Svensson .......... A61L 29/043 604/544 |
| 2011/0114520 A1 | 5/2011 | Matthison-Hansen |
| 2011/0125135 A1 | 5/2011 | Ahmed |
| 2011/0160662 A1 | 6/2011 | Stout |
| 2011/0178425 A1 | 7/2011 | Nishtala |
| 2011/0212157 A1 | 9/2011 | Edelson et al. |
| 2011/0238163 A1 | 9/2011 | Andrews et al. |
| 2011/0268938 A1 | 11/2011 | Schuhmann |
| 2012/0035530 A1 | 2/2012 | Wang |
| 2012/0121919 A1 | 5/2012 | Nielsen |
| 2013/0006226 A1* | 1/2013 | Hong ............. A61M 25/0017 604/544 |
| 2013/0131646 A1 | 5/2013 | Gilman |
| 2013/0345681 A1 | 12/2013 | Hong |

FOREIGN PATENT DOCUMENTS

| | | |
|---|---|---|
| DE | 10 2011 119160 A1 | 5/2013 |
| EP | 0010171 A1 | 4/1980 |
| EP | 0166998 B1 | 1/1986 |
| EP | 0613672 A1 | 9/1994 |
| EP | 0628586 B1 | 12/1994 |
| EP | 0692276 A2 | 1/1996 |
| EP | 1062920 A1 | 12/2000 |
| EP | 1110561 A2 | 6/2001 |
| EP | 1415671 A1 | 5/2004 |
| EP | 2301595 A1 | 3/2011 |
| EP | 2520412 A1 | 11/2012 |
| EP | 2609956 A1 | 7/2013 |
| GB | 2083762 | 3/1982 |
| GB | 2496901 A | 5/2013 |
| JP | S-61209655 A | 9/1986 |
| JP | 01-136662 | 9/1989 |
| JP | 11151293 | 6/1999 |
| KR | 2000/065291 A | 11/2000 |
| KR | 100754057 B | 8/2007 |
| WO | WO 89/05671 A | 6/1989 |
| WO | WO 96/41653 A1 | 12/1996 |
| WO | WO 1998/058989 A1 | 12/1998 |
| WO | WO 00/30696 A1 | 6/2000 |
| WO | WO 2006/055847 A2 | 5/2006 |
| WO | WO 2006/071813 A2 | 7/2006 |
| WO | WO 2007/122269 A1 | 11/2007 |
| WO | WO 2007/140320 A2 | 12/2007 |
| WO | WO 2007/142579 | 12/2007 |
| WO | WO 2010/043565 A1 | 4/2010 |
| WO | WO 2011/076211 A1 | 6/2011 |
| WO | WO 2012/163413 A1 | 12/2012 |
| WO | WO 2012/166967 A1 | 12/2012 |
| WO | WO 2014/193402 A1 | 12/2014 |

OTHER PUBLICATIONS

Beom Soo Kim, Jeffrey S. Hrkach, Robert Langer, Biodegradable photo-crosslinked poly(ether-ester) networks for lubricious coatings, Biomaterials, vol. 21, Issue 3, Feb. 2000, pp. 259-265.

A.K. Singla, M. Chawla, Chitosan some pharmaceutical and biological aspects, an update, Journal of Pharmacy and Pharmacology, Aug. 2001, 53: 1047-1067.

FreeStyle Vie Flushable Colostomy Bag by CliniMed Ltd., retrieved from http://www.clinimed.co.uk/Stoma-Care/Products/Closed-Stoma-Bags/Freestyle-Vie-Flushable/Product-Design.aspx Jan. 1, 2014.

International Search Report and Written Opinion dated Jun. 10, 2015, for International Application No. PCT/US2014/069508.

* cited by examiner

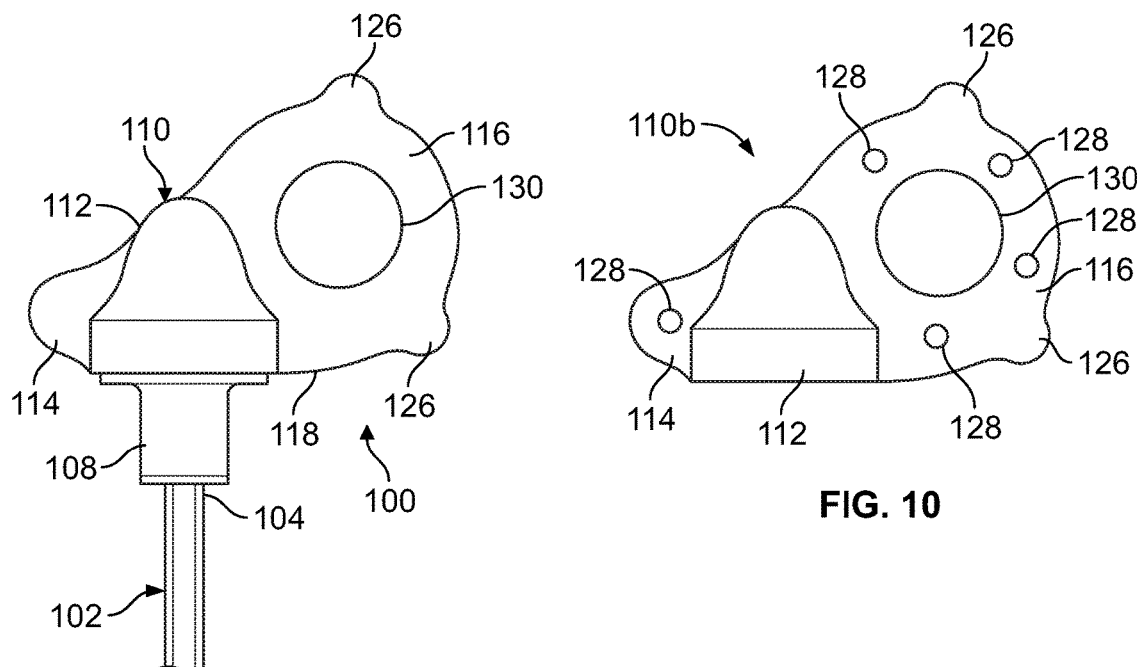
FIG. 8
FIG. 10
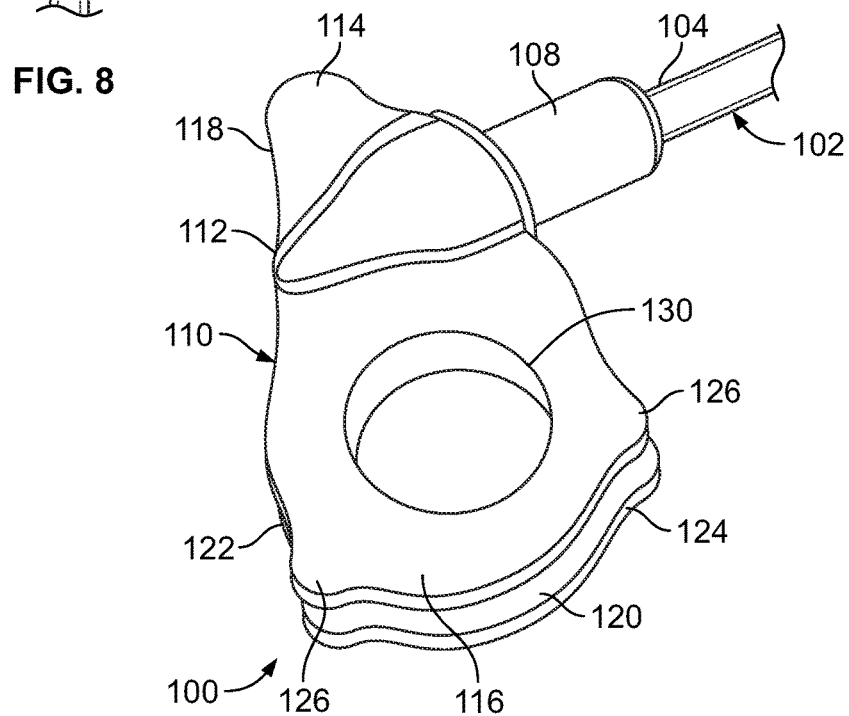
FIG. 9

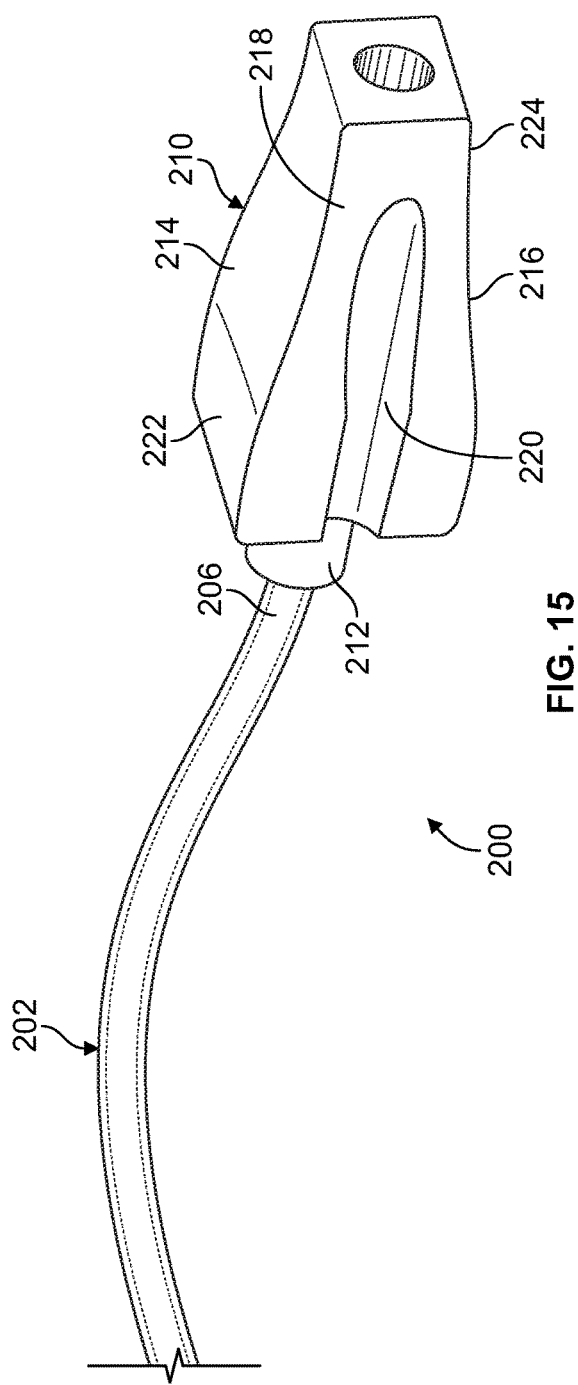
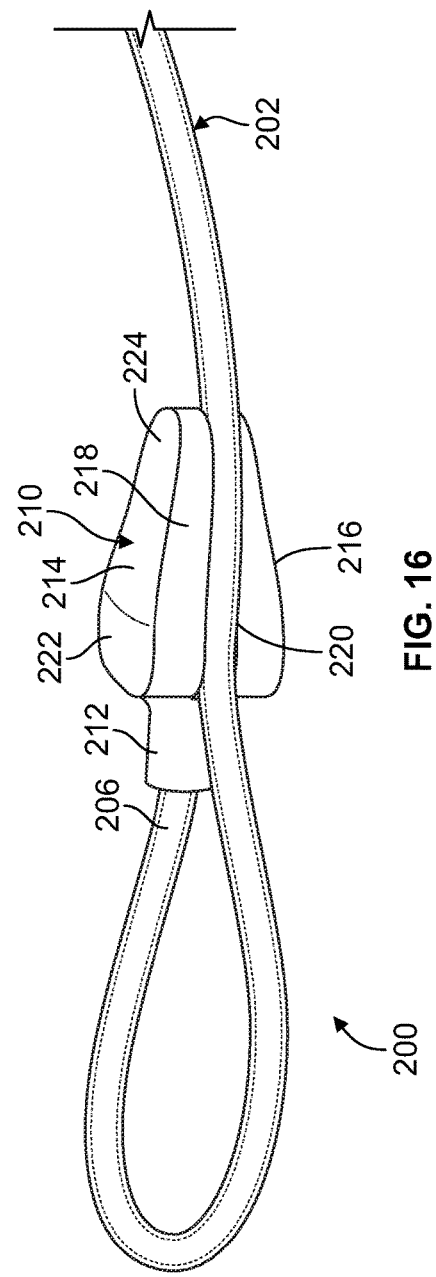
FIG. 15
FIG. 16

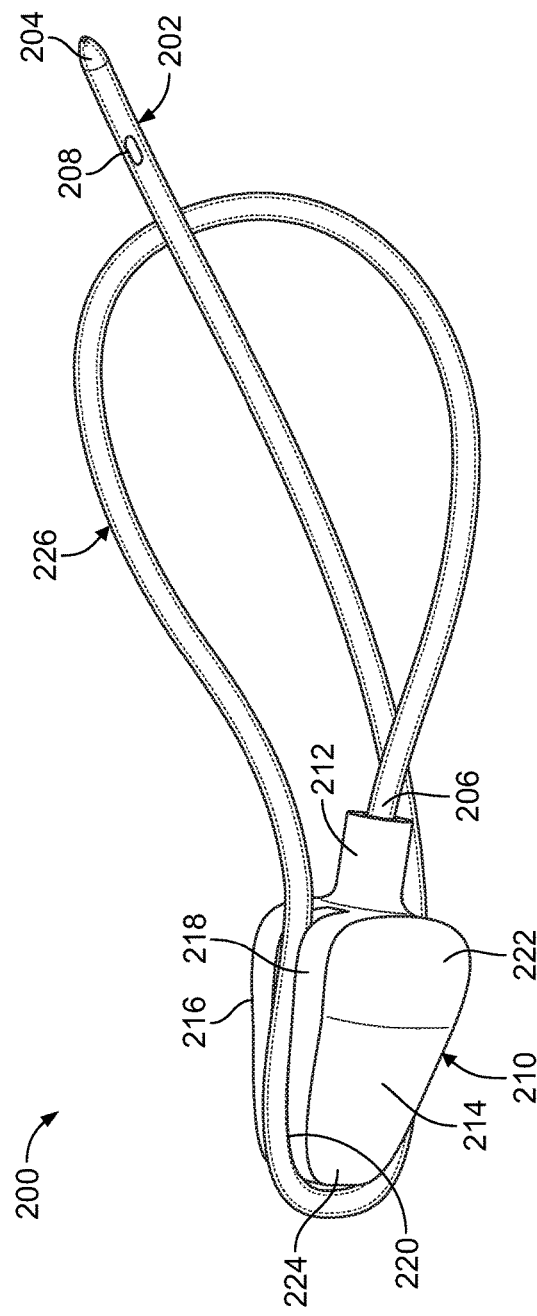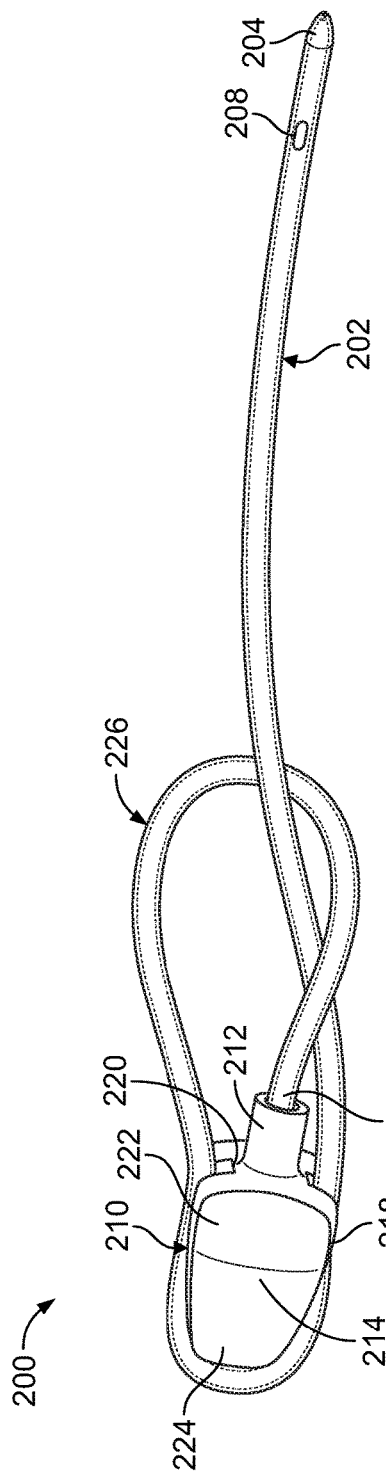

FLUSHABLE CATHETERS

RELATED APPLICATIONS

This application is a U.S. national stage application of PCT Patent Application Serial No. PCT/US2014/069508, filed Dec. 10, 2014, which claims the benefit of and priority of U.S. Provisional Patent Application Ser. No. 61/915,220, filed Dec. 12, 2013; U.S. Provisional Patent Application Ser. No. 62/011,078, filed Jun. 12, 2014; and U.S. Provisional Patent Application Ser. No. 61/915,396, filed Dec. 12, 2013, the contents of all of which are incorporated by reference herein.

DESCRIPTION

Technical Field

The present disclosure generally relates to catheters. More particularly, the present disclosure relates to flushable catheters.

Background

Intermittent catheters are commonly used by those who suffer from various abnormalities of the urinary system, such as urinary incontinence. With the advent of intermittent catheters, individuals with urinary system abnormalities can self-insert and self-remove intermittent catheters several times a day. Intermittent catheterization involves inserting the elongated shaft of a catheter through the urethra and into the bladder. Urine is drained from the bladder through the catheter and into a waste receptacle, such as a toilet or collection bag.

After the bladder has been drained, the catheter is disposed of in a waste container, such as a garbage can. Sometimes, especially in a public restroom having multiple stalls in which there is no garbage can present in the individual stalls, it may be difficult to find a suitable waste container to dispose of the catheter and, if the individual has to carry the catheter some distance to a waste container, there may be some risk of leakage or spillage of bodily fluids. Additionally, the individual, especially in a public restroom, may be uncomfortable or embarrassed with carrying a used catheter to the waste container. In such situations, the individual may attempt to dispose of the catheter by flushing it down the toilet, which can cause significant plumbing problems, such as clogging. This is especially problematic for male users, as male urinary catheters are typically much longer than female urinary catheters, due to anatomical considerations. Such catheters are typically made from non-biodegradable polymeric materials, such as non-biodegradable thermoplastics, in which case flushing the catheter down the toilet also raises environmental concerns.

Accordingly, there has been increasing interest in producing flushable catheters which are made from materials that structurally degrade when contacted with water, e.g., materials that are soluble in water and/or undergo hydrolysis. Such catheters are intended to be flushed down the toilet after use and degrade or breakdown while passing through the sanitary system. Because flushable catheters are required to substantially maintain structural integrity during use (i.e., during insertion into the urethra, drainage of urine, and removal from the urethra), the degradable materials typically chosen are those with a slower degradation rate, in which case the catheter does not substantially degrade until after being disposed of in the sanitary system for some time. Thus, when a flushable catheter is placed within the toilet for disposal, the structure of the catheter usually is still substantially intact and will remain substantially intact during flushing of the catheter for disposal thereof.

When a catheter is disposed of by flushing down a toilet, the force of the turbulent water current which occurs during flushing oftentimes does not carry or move the catheter down the toilet and into the pipes of the sanitary system and the catheter remains in the toilet bowl after flushing. The catheter may not flush down the toilet for any number of reasons. For example, if the catheter is too buoyant, it may float to the top of the toilet water, which may make it difficult for the flushing water to carry the catheter down the toilet. Conversely, if the catheter is not buoyant enough, it may sink to the bottom of the toilet, which may also make it difficult for flushing water to carry the catheter down the toilet. Additionally, because of the geometry of a typical urinary catheter, the force or energy of the flushing water may not sufficiently impinge on the catheter to propel it down the toilet. This may be especially problematic with water-conserving low-flush or low-flow toilets. Regardless of the reason, a catheter that resists being fully flushed down the toilet may require the user to flush the toilet multiple times or leave the catheter in the toilet, which may be embarrassing, especially when using a public restroom.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a flushable catheter assembly includes a catheter shaft having proximal and distal end portions, with a funnel assembly associated with the distal end portion of the catheter shaft. A drainage portion is defined through the funnel assembly, with the funnel assembly also including a groove along at least a portion of its outer perimeter and/or a shaft channel defined through the funnel assembly. The groove and/or shaft channel is configured to receive at least a portion of the catheter shaft for securing the catheter shaft to the funnel assembly for disposal.

In another aspect, a flushable catheter assembly includes a catheter shaft having proximal and distal end portions, with an introducer tip associated with the proximal end portion of the catheter shaft and an introducer cap assembly removably connected to the introducer tip. The introducer cap assembly defines a groove along at least a portion of its outer perimeter, with the groove being configured to receive at least a portion of the catheter shaft for wrapping the catheter shaft around the outer perimeter of the introducer cap assembly.

In yet another aspect, a method is provided for disposing of a catheter assembly of the type having a catheter shaft and a funnel assembly associated with a distal end portion of the catheter shaft. The method includes securing at least a portion of the catheter shaft to the funnel assembly, which may be achieved by wrapping at least a portion of the catheter shaft around the outer perimeter of the funnel assembly, with at least part of the catheter shaft positioned within a groove defined along at least a portion of the outer perimeter, and/or passing at least part of the catheter shaft through a shaft channel defined through the funnel assembly. With the catheter shaft so secured, the catheter assembly is then placed in a waste container.

In another aspect, a method is provided for disposing of a catheter assembly of the type having a catheter shaft and an introducer cap assembly associated with a proximal end portion of the catheter shaft. The method includes wrapping at least a portion of the catheter shaft around an outer perimeter of the introducer cap assembly, with the catheter shaft positioned within a groove defined along at least a portion of the outer perimeter. The catheter assembly is then placed in a waste container, with the catheter shaft positioned within the groove.

BRIEF DESCRIPTION OF THE DRAWINGS

FIG. 8 is a front elevational view of an embodiment of a cap assembly of a urinary catheter according to an aspect of the present disclosure;

FIG. 9 is a perspective view of the cap assembly of FIG. 8;

FIG. 10 is a front elevational view of a variation of the cap assembly of FIG. 8;

FIG. 15 is a perspective view of an alternative embodiment of a funnel assembly of a flushable catheter assembly according to an aspect of the present disclosure;

FIGS. 16-18 are perspective views illustrating a catheter shaft being wrapped around the funnel assembly of FIG. 15 for improved disposability;

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
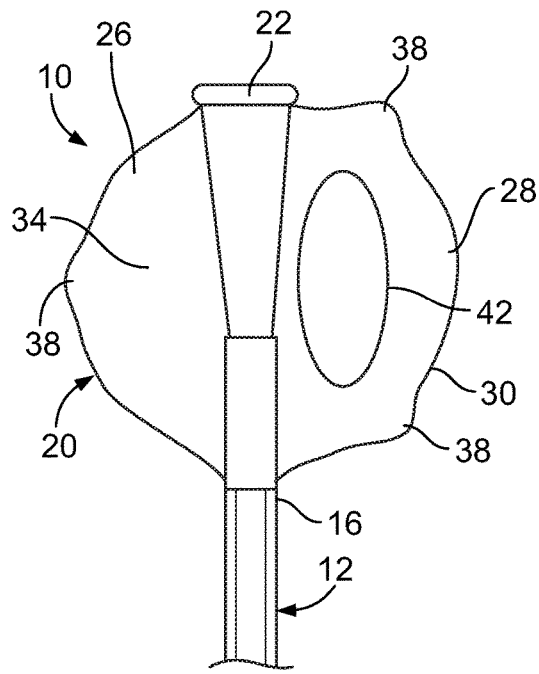
FIG. 1 is a front elevational view of an embodiment of a funnel assembly of a urinary catheter according to an aspect of the present disclosure.
Figure 2:
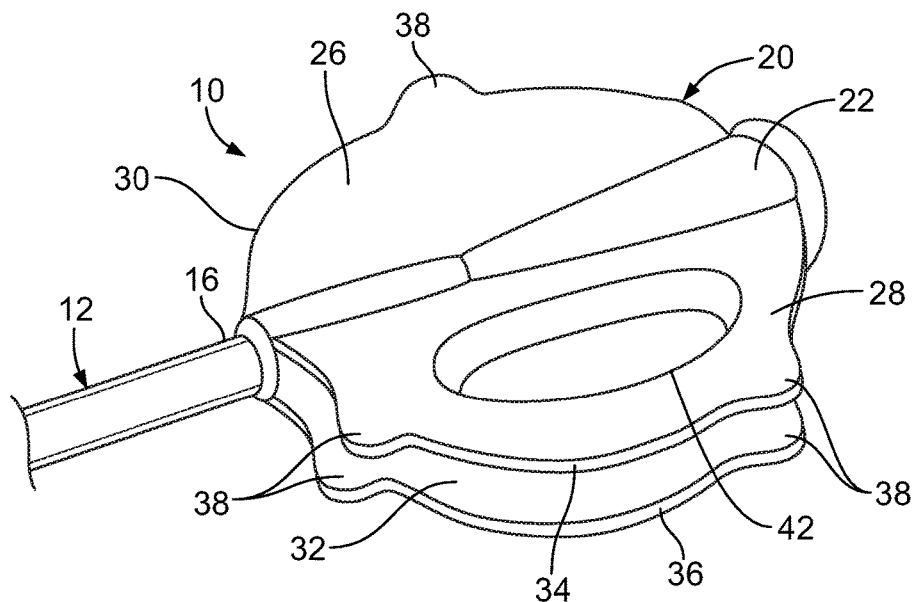
FIG. 2 is a perspective view of the funnel assembly of FIG. 1.

FIGS. 1 and 2 show an embodiment of a catheter assembly 10 according to an aspect of the present disclosure. The catheter assembly 10 includes an elongated catheter shaft 12 having a proximal end portion 14 (FIGS. 4 and 5) and a distal end portion 16. The proximal end portion 14 of the catheter shaft 12 is suitable for insertion into a lumen or a passageway of the body, such as the urethra. The proximal end portion 14 may include one or more draining holes or eyes 18 for the drainage of bodily fluids therethrough and into an internal conduit or lumen of the catheter shaft 12.

Fluid entering the catheter shaft 12 via the eye 18 flows from the proximal end portion 14 to the distal end portion 16. The distal end portion 16 may include an associated drainage member or funnel assembly 20 for fluidly connecting the flow path defined by the catheter shaft 12 to a collection container, such as a collection bag, or for directing urine into a waste container, such as a toilet.

The catheter assembly 10 and all of the other catheter assemblies described herein are preferably, but not necessarily, of the type that structurally break down when contacted by water for convenient disclosure down the toilet and through the sewer system. The catheter assemblies described herein may be made from one or more materials that are affected by a fluid (for example, water, urine, or fluids utilized in toilet and plumbing systems). Such materials may be water disintegratable or disintegrable materials. As used herein, the terms "water disintegratable" and "water disintegrable" refer to materials that are water soluble, water degradable, or water hydrolysable, and which dissolve, degrade, or otherwise break down when in contact with water over a selected period of time. In other embodiments, the material may be enzymatically hydrolysable. The water disintegrable and enzymatically hydrolysable materials are preferably flushable materials which are suitable for disposal in a toilet or sanitary system and, even more preferably, biodegradable flushable materials which may be chemically broken down by living organisms or other biological means.

Such water disintegrable or enzymatically hydrolysable materials may include, for example, polyvinyl alcohol, including but not limited to an extrudable polyvinyl alcohol, polyacrylic acids, polyactic acid, polyesters, polyglycolide, polyglycolic acid, poly lactic-co-glycolic acid, polylactide, amines, polyacrylamides, poly(N-(2-Hydroxypropyl)methacrylamide), starch, modified starches or derivatives, amylopectin, pectin, xanthan, scleroglucan, dextrin, chitosans, chitins, agar, alginate, carrageenans, laminarin, saccharides, polysaccharides, sucrose, polyethylene oxide, polypropylene oxide, acrylics, polyacrylic acid blends, poly(methacrylic acid), polystyrene sulfonate, polyethylene sulfonate, lignin sulfonate, polymethacrylamides, copolymers of aminoalkyl-acrylamides and methacrylamides, melamine-formaldehyde copolymers, vinyl alcohol copolymers, cellulose ethers, poly-ethers, polyethylene oxide, blends of polyethylene-polypropylene glycol, carboxymethyl cellulose, guar gum, locust bean gum, hydroxyproply cellulose, vinylpyrrolidone polymers and copolymers, polyvinyl pyrrolidone-ethylene-vinyl acetate, polyvinyl pyrrolidone-carboxymethyl cellulose, carboxymethyl cellulose shellac, copolymers of vinylpyrrolidone with vinyl acetate, hydroxyethyl cellulose, gelatin, poly-caprolactone, poly(p-dioxanone), or combinations, blends, or co-polymers of any of the above materials. The water disintegrable materials may also be any of those that are included in certified flushable products that meet the National Sanitation Foundation standards for flushability or materials and products that meet INDA/EDANA Flushability Guidelines or the UK Water Industry Research test protocols set forth in "Test Protocol to Determine the Flushability of Disposable Products, Review of the Manufactures $3^{rd}$ Ed. Guidance Document," 2013, by Drinkwater et al. While catheters made from water disintegrable materials may be disposed of in a toilet, it is not necessary to dispose of such catheters in a toilet and such catheters may also be disposed in normal municipal waste systems or garbage collection systems.

The funnel assembly 20 (which may be formed of one or more of the materials listed above) may include a hollow, generally frusto-conical drainage portion 22, which may be shaped according to conventional design (see, e.g., the funnel 24 of FIGS. 11 and 12) and be configured to drain fluid from the catheter shaft 12. The funnel drainage portion 22 may be positioned between a pair of lateral portions 26 and 28, which define an outer perimeter 30 of the funnel assembly 20. In the illustrated embodiment, the lateral portions 26 and 28 of the funnel assembly 20 are generally semicircular, but it is within the scope of the present disclosure for the lateral portions 26 and 28 and, hence, the outer perimeter 30 of the funnel assembly 20, to be differently shaped. Further, it is within the scope of the present disclosure for there to be only one lateral portion associated with the funnel drainage portion 22.

The funnel assembly 20 may include one or more wrapping and/or holding features to aid in compacting the catheter assembly 10 for placement into a waste container, such as a toilet. For example, in the illustrated embodiment, at least a portion of the outer perimeter 30 of the funnel assembly 20 defines a groove 32 (FIGS. 2 and 5), positioned between front and rear faces 34 and 36 of the lateral portions 26 and 28 of the funnel assembly 20. In the illustrated embodiment, the front and rear faces 34 and 36 are substantially parallel at least in the vicinity of the groove 32, such that the groove 32 is defined between substantially parallel surfaces. The groove 32 is preferably configured to receive at least a portion of the catheter shaft 12 when the catheter shaft 12 is wrapped around the funnel assembly 20 (FIGS. 4 and 5), as will be described in greater detail. Accordingly, the width of the groove 32 (i.e., the distance between the faces 34 and 36) is preferably at least as great as the diameter of the catheter shaft 12, to allow the catheter shaft 12 to be received within the groove 32. Alternatively, the width of the groove 32 may be less than the diameter of the catheter shaft 12, in which case the catheter shaft 12 may be only partially positioned within the groove 32. It is also within the scope of the present disclosure for the width of the groove 32 to vary along the outer perimeter 30 of the funnel assembly 20.

The depth of the groove 32 (i.e., the dimension in the radial direction) may be either substantially uniform or vary along the outer perimeter 30 of the funnel assembly 20. In one embodiment, at least a portion of the groove 32 may have a depth greater than or equal to the diameter of the catheter shaft 12, such that the corresponding portion of the catheter shaft 12 may be fully received within the groove 32 when the catheter shaft 12 is wrapped around the funnel assembly 20. However, it is also within the scope of the present disclosure for all or a portion of the groove 32 to have a depth less than the diameter of the catheter shaft 12, such that the catheter shaft 12 is only partially received within the groove 32 when wrapped around the funnel assembly 20.

In the illustrated embodiment, the faces 34 and 36 of the lateral portions 26 and 28 combine to define a groove 32 (best seen in FIGS. 2 and 5) having a substantially uniform depth, except at selected locations. In the embodiment of FIGS. 1 and 2, each face 34, 36 includes one or more extensions 38, with the depth of the groove 32 being greater in the vicinity of the extensions 38. In the illustrated embodiment, the faces 34 and 36 are substantially identical, such that each extension 38 is aligned with an extension 38 of the other face 34, 36. The extensions 38 may help to retain the catheter shaft 12 within the groove 32, such that the depth of the groove 32 at other locations may be relatively small (e.g., less than the diameter of the catheter shaft 12) or non-existent without risking the wrapped catheter shaft 12 disengaging from the funnel assembly 20. Decreasing the depth of the groove 32 or eliminating the groove 32 in selected locations may be advantageous in that less material is required to form the funnel assembly 20 (because the faces 34 and 36 may be smaller overall), thereby decreasing the cost of the catheter assembly 10 and increasing the speed at which the funnel assembly 20 deteriorates or dissolves in water. Additionally, the extensions 38, if provided, may serve as gripping surfaces or elements for a user during use of the catheter assembly 10 for improved handling and manipulation.

Figure 3:
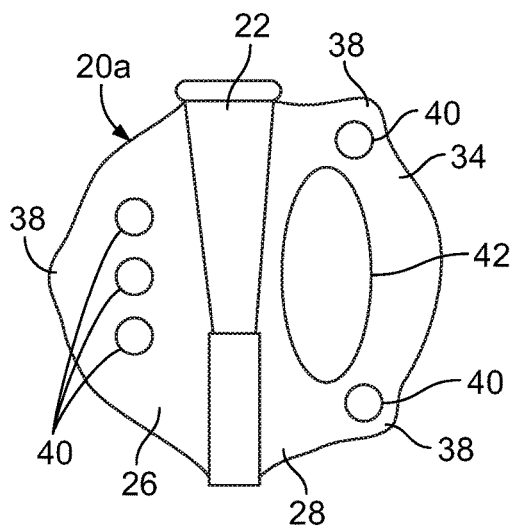
FIG. 3 is a front elevational view of a variation of the funnel assembly of FIG. 1.

The diameter of the faces 34 and 36 of the lateral portions 26 and 28 is increased at the locations of the extensions 38, which may be advantageous in allowing for the incorporation of additional features. For example, in an alternative embodiment shown in FIG. 3, at least one extension 38 of the funnel assembly 20*a* has a hole 40 associated therewith. The hole 40 may pass through the funnel assembly 20*a* from the front face 34 to the rear face 36, which increases the surface area of the funnel assembly 20*a*. This may be advantageous by increasing the amount of surface area contacted by moving water when the catheter assembly 10 is flushed down a toilet (as will be described in greater detail), which may assist in moving the catheter assembly 10 through a wastewater drainage pipe. Additionally, exposing more surface area to water will increase the speed at which the funnel assembly 20*a* deteriorates or dissolves in water. In the illustrated embodiment, one of the lateral portions 28 includes two extensions 38, with each extension 38 having a hole 40 associated therewith. As for the other lateral portion 26, it is illustrated with three holes 40 arranged in a line or row spaced away from the extension 38. Hence, it can be seen that a hole 40 passing through all or a portion of the funnel assembly 20*a* may be associated with an extension 38 or located at a different area. It should be understood that the illustrated configuration is merely exemplary, and it is within the scope of the present disclosure for the funnel assembly 20*a* to include fewer or more holes 40 than the number illustrated and/or for the holes 40 to be differently shaped, arranged, and oriented.

As shown in the embodiments of FIGS. 1-5, the funnel assembly 20, 20*a* may define an opening 42 sized and oriented to receive at least one digit or finger of a user. If provided, a user may insert at least a portion of a digit into the opening 42 to grip the funnel assembly 20, 20*a*, which may be advantageous when handling the catheter assembly 10 (e.g., while advancing the catheter shaft 12 into the urethra and/or withdrawing the catheter shaft 12 from the urethra). The opening 42 may provide improved handling during other times as well, such as removing the catheter assembly 12 from a package or disposing of the catheter assembly 10. Additionally, the opening 42 may serve to receive the proximal end portion 14 of the catheter shaft 12 (FIGS. 4 and 5) after use. In particular, the catheter shaft 12 may be wrapped around the funnel assembly 20, 20*a*, with a portion of the catheter shaft 12 positioned within the groove 32 to define an at least partial loop. The proximal end portion 14 may then be passed through the loop via the opening 42 in the funnel assembly 20, 20*a* to effectively tie the catheter shaft 12 in a simple knot, which retains the catheter shaft 12 on the funnel assembly 20, 20*a* in a compact orientation. The compact orientation of FIGS. 4 and 5 decreases the footprint and compacts the mass of the catheter assembly 10, which may improve movement of the catheter assembly 10 through a wastewater drainage pipe when flushed down a toilet.

Figure 5:
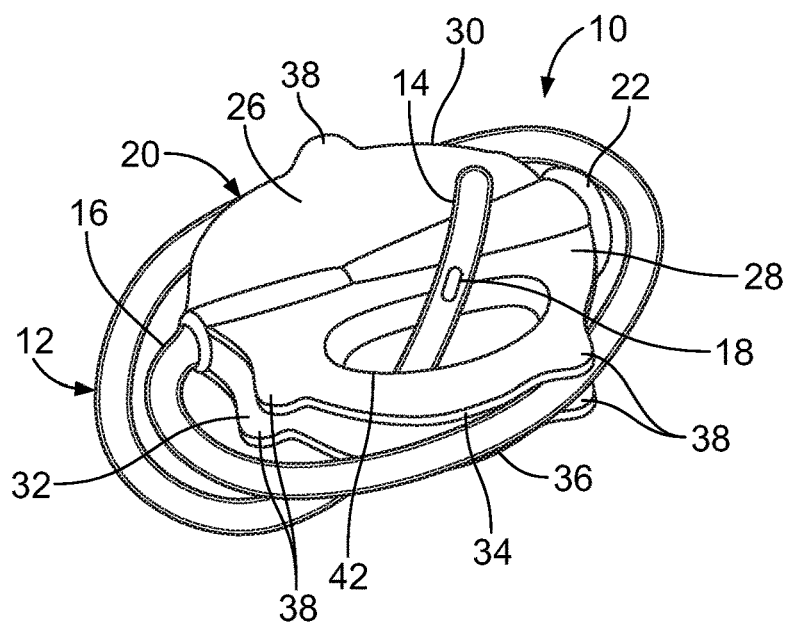
FIG. 5 is a perspective view of the catheter shaft and funnel assembly of FIG. 4.
Figure 6:
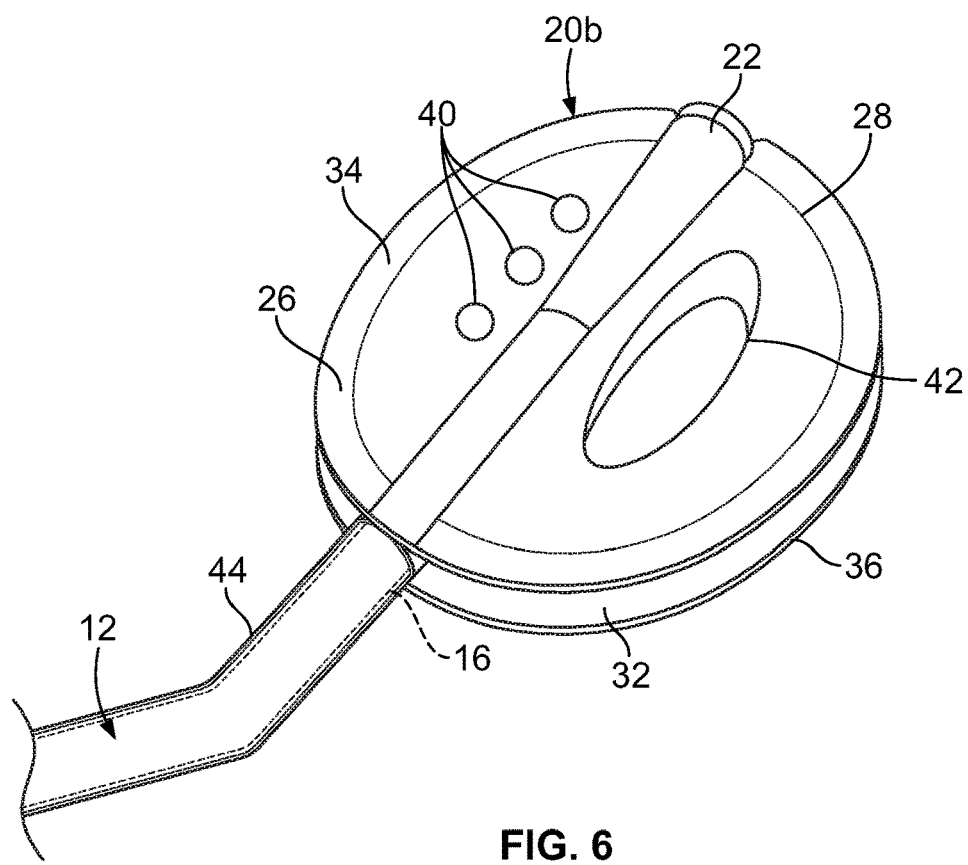
FIG. 6 is a perspective view of an alternative embodiment of a funnel assembly of a urinary catheter according to an aspect of the present disclosure.
Figure 7:
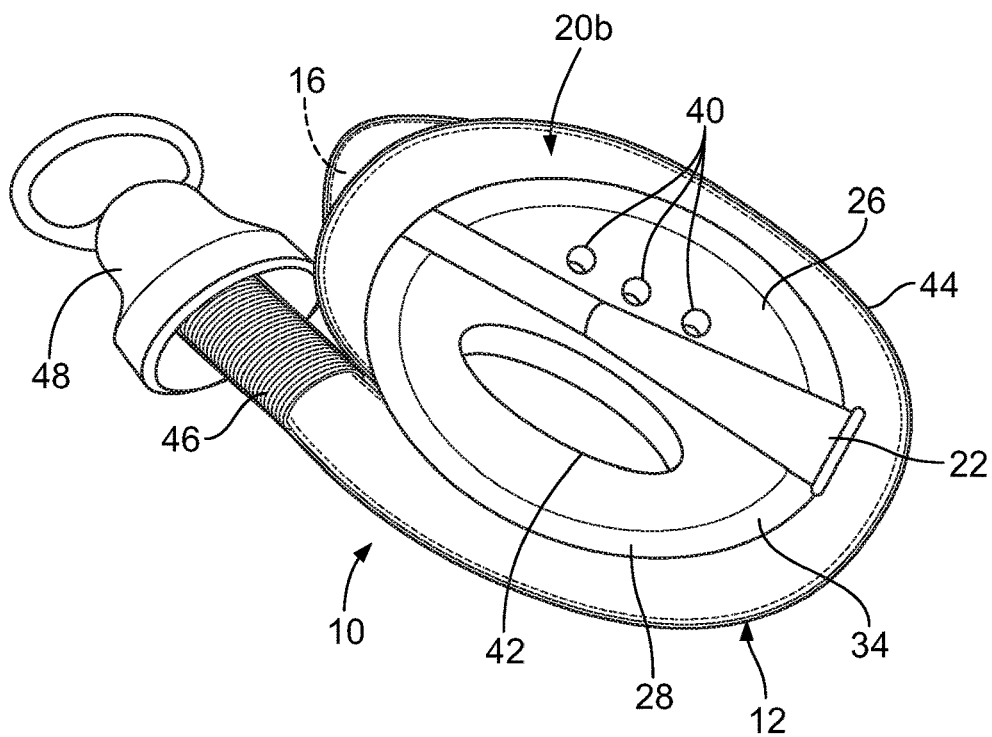
FIG. 7 is a perspective view of a catheter shaft wrapped around the funnel assembly of FIG. 6.

FIGS. 6 and 7 illustrate another embodiment of a funnel assembly 20*b* according to the present disclosure. The funnel assembly 20*b* of FIGS. 6 and 7 is similar to the embodiment of FIG. 3, but it omits any extensions 38 and instead has a more uniform circular or ovoid or oblong outer diameter. On account of omitting extensions 38, the funnel assembly 20*b* of FIGS. 6 and 7 includes holes 40 on one lateral portion 26, but not the other 28, due to there being less room between the opening 42 and the outer perimeter of the lateral portion 28. The smoother, more uniform outer perimeter shown in FIGS. 6 and 7 is an exemplary alternative to the perimeter 30 of the embodiments of FIGS. 1-5, but it should be understood that other configurations and perimeter shapes may also be employed without departing from the scope of the present disclosure.

Turning now to an exemplary method of using the catheter assembly 10 for draining the bladder of a male, it is first removed from a package, if provided. When free of its package, the proximal end portion 14 may be advanced into the urethra. If the catheter shaft 12 is not formed of an inherently lubricious material or provided with a lubricious coating, it may be preferred to apply a lubricant to the outer surface of the catheter shaft 12 for improved comfort as the user advances the catheter shaft 12 through the urethra to the bladder. The catheter shaft 12 may be housed within a protective sleeve 44, as in the embodiment of FIGS. 6 and 7, to shield it from the outside environment prior to advancement into the urethra or it may be uncovered, as in FIGS. 1-5. Additionally, after the catheter assembly 10 has been used, the protective sleeve 44 may be used to handle the catheter shaft 12 without directly contacting the catheter shaft 12, as will be described in greater detail herein.

The catheter assembly 10 may include an introducer tip 46 (FIG. 7) according to conventional design, with the end of the catheter shaft 12 initially positioned within the introducer tip 46 to maintain sterility. The introducer tip 46 itself may be positioned within a removable cap 48 (FIG. 7) prior to use to maintain sterility of the introducer tip 46. If provided, the cap 48 is removed from the introducer tip 46 just prior to use, with a portion of the introducer tip 46 being advanced into the urethra. With the introducer tip 46 partially positioned within the urethra, the catheter shaft 12 may be moved proximally with respect to the introducer tip 46 to advance the proximal end portion 14 of the catheter shaft 12 out of the introducer tip 46 and into the urethra without exposing the end of the catheter shaft 12 to the outside environment.

When the catheter shaft 12 has been advanced into the urethra to the point that the eyes 18 are positioned within the bladder, urine from the bladder will flow into the eyes 18, through the catheter shaft 12 and to the distal end portion 16 of the catheter shaft 12. The urine exits the catheter assembly 10 via the drainage portion 22 of the funnel assembly 20, into a collection container (e.g., a urine collection bag that may be formed of a flushable, fluid-disintegrable material) or a disposal device (e.g., a toilet). Thereafter, the user may grip the funnel assembly 20 (e.g., by placing a digit through or partially into the opening 42) and move the funnel assembly 20 distally away from the body to withdraw the catheter shaft 12 and introducer tip 46 (if provided) from the urethra.

Figure 4:
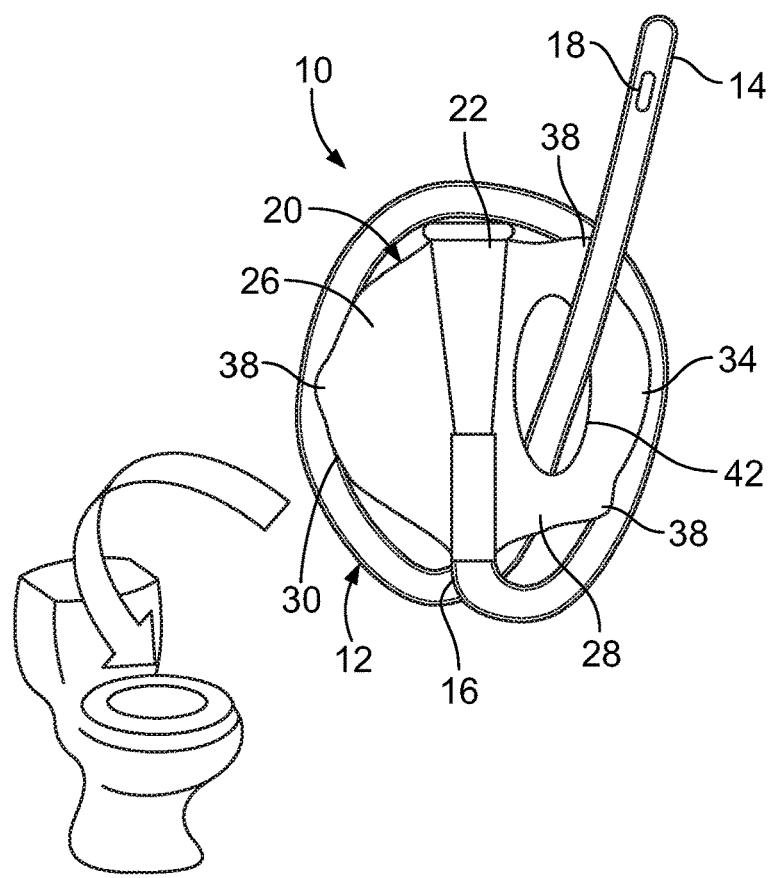
FIG. 4 is a front elevational view of a catheter shaft wrapped around the funnel assembly of FIG. 1 for improved disposability.

Following use, the catheter shaft 12 may be wrapped around the funnel assembly 20 to provide a more compact configuration for disposal (FIGS. 4-5 and 7). If a protective sleeve 44 is associated with the catheter shaft 12, the catheter shaft 12 may be retracted into or otherwise repositioned within the protective sleeve 44 after use, which allows a user to handle the protective sleeve 44, rather than the catheter shaft 12 itself. This may be advantageous, in that the protective sleeve 44 remains outside of the body during use, so it may be more hygienically handled than the catheter shaft 12 when wrapping the catheter shaft 12 around the funnel assembly 20. If the funnel assembly 20 includes an opening 42, the proximal end portion 14 may be passed through the opening 42 after the catheter shaft 12 has been looped around the funnel assembly 20 to effectively tie the catheter shaft 12 in a simple knot to retain the catheter shaft 12 in the compact, wrapped or looped or coiled orientation (FIGS. 4 and 5).

With the catheter assembly 10 in a compact configuration, it may be disposed of by any suitable means. Most notably, the catheter assembly 10 may be flushed down a toilet, with the compact configuration aiding passage of the catheter assembly 10 through the sewage system. As described above, the catheter shaft 12 and other components of the catheter assembly 10 may be formed of a water disintegrable material to cause the catheter assembly 10 to break down as it passes through the sewage system. The funnel assembly 20 is preferably formed of a water disintegrable material and/or an activation agent material configured to aid in the breakdown of the catheter assembly 10 in water. By way of example, the combination of sodium bicarbonate (incorporated into the catheter shaft 12 or the funnel assembly 20) and acetic acid (incorporated into the other one of the catheter shaft 12 or the funnel assembly 20) in water creates a bubbling effect which increases the speed at which the catheter assembly 10 will break down after being placed into a toilet.

FIGS. 8-14 illustrate embodiments of catheter assemblies having introducer cap assemblies which aid in the compacting and disintegration of a fully flushable catheter shaft.

In the embodiment of FIGS. 8 and 9, a catheter assembly 100 includes an elongated catheter shaft 102 which may be either differently configured or substantially identical to the catheter shaft 12 described above. In the illustrated embodiment, the proximal end portion 104 of the catheter shaft 102, which is illustrated as being at least partially positioned within an associated introducer tip 108, may be substantially identical to the proximal end portion 14 of FIGS. 4 and 5. Fluid entering the catheter shaft 102 via an eye of the proximal end portion flows from the proximal end portion 104 to the distal end portion 106. The distal end portion 106 may include an associated drainage member or funnel 24 for fluidly connecting the flow path defined by the catheter shaft 102 to a collection container, such as a collection bag, or for directing urine into a waste container, such as a toilet. It is also within the scope of the present disclosure for catheter assemblies of the type shown in FIGS. 8-14 to be provided with funnel assemblies of the type described above. As will be described in greater detail, the introducer cap assemblies of FIGS. 8-14 perform many of the functions of the funnel assemblies of FIGS. 1-7, so it may be preferred for the catheter assemblies of FIGS. 8-14 to be provided with a standard funnel 24, as illustrated, which may be smaller than the funnel assemblies of FIGS. 1-7.

As described above in greater detail with respect to the catheter shaft 12, the catheter shaft 102 is preferably, but not necessarily, made from one or more water disintegrable materials which break down when in contact with water.

The catheter assembly 100 further includes an introducer cap assembly 110. The introducer cap assembly 110 may include a hollow cap portion 112, which is configured to receive at least a proximal end or portion of the introducer tip 108. The illustrated cap portion 112 is generally bell-shaped, which may be advantageous when used in combination with a conventional introducer tip, but the shape of the cap portion 112 may vary without departing from the scope of the present disclosure. Preferably, the cap portion 112 is configured to be detachably connected to the introducer tip 108, such that the introducer cap assembly 110 may be removed from introducer tip 108 during use and then reconnected following use, as will be described in greater detail.

The cap portion 112 may be positioned between a pair of lateral portions 114 and 116, which define an outer perimeter 118 of the introducer cap assembly 110. In the illustrated embodiment, the lateral portions 114 and 116 are differently shaped, with one lateral portion 116 also being larger than the other lateral portion 114, but it is also within the scope of the present disclosure for the lateral portions 114 and 116 to be substantially the same size and/or shape. Additionally, while the illustrated embodiment includes one generally semi-circular lateral portion 116 and one generally circular or annular lateral portion 116, the lateral portions may be differently shaped without departing from the scope of the present disclosure. Similarly, while the illustrated lateral portions 114 and 116 of the introducer cap assembly 110 combine to define a generally triangular perimeter 118, it is within the scope of the present disclosure for the lateral portions 114 and 116 to combine to define a differently shaped perimeter. Further, it is within the scope of the present disclosure for there to be only one lateral portion associated with the cap portion 112.

The introducer cap assembly 110 may include one or more wrapping and/or holding features to aid in compacting the catheter assembly 100 for placement into a waste container, such as a toilet. For example, in the illustrated embodiment, at least a portion of the outer perimeter 118 of the introducer cap assembly 110 defines a groove 120 (FIGS. 9 and 12), positioned between front and rear faces 122 and 124 of the lateral portions 114 and 116 of the introducer cap assembly 110. In the illustrated embodiment, the front and rear faces 122 and 124 are substantially parallel at least in the vicinity of the groove 120, such that the groove 120 is defined between substantially parallel surfaces. The groove 120 is preferably configured to receive at least a portion of the catheter shaft 102 when the catheter shaft 102 is wrapped around the introducer cap assembly 110 (FIGS. 11 and 12), as will be described in greater detail. Accordingly, the width of the groove 120 (i.e., the distance between the faces 122 and 124) is preferably at least as great as the diameter of the catheter shaft 102, to allow the catheter shaft 102 to be received within the groove 120. Alternatively, the width of the groove 120 may be less than the diameter of the catheter shaft 102, in which case the catheter shaft 102 may be only partially positioned within the groove 120. It is also within the scope of the present disclosure for the width of the groove 120 to vary along the outer perimeter 118 of the introducer cap assembly 110.

The depth of the groove 120 (i.e., the dimension in the radial direction) may be either substantially uniform or vary along the outer perimeter 118 of the introducer cap assembly 110. In one embodiment, at least a portion of the groove 120 may have a depth greater than or equal to the diameter of the catheter shaft 102, such that the corresponding portion of the catheter shaft 102 may be fully received within the groove 120 when the catheter shaft 102 is wrapped around the introducer cap assembly 110. However, it is also within the scope of the present disclosure for all or a portion of the groove 120 to have a depth less than the diameter of the catheter shaft 102, such that the catheter shaft 102 is only partially received within the groove 120 when wrapped around the introducer cap assembly 110.

In the illustrated embodiment, the faces 122 and 124 of the lateral portions 114 and 116 combine to define a groove 120 having a substantially uniform depth, except at selected locations. In the embodiment of FIGS. 8 and 9, at least one of the faces 122, 124 includes one or more extensions 126, with the depth of the groove 120 being greater in the vicinity of the extensions 126. In the illustrated embodiment, the faces 122 and 124 are substantially identical, such that each extension 126 is aligned with an extension 126 of the other face 122, 124. The extensions 126 may help to retain the catheter shaft 102 within the groove 120, such that the depth of the groove 120 at other locations may be relatively small (e.g., less than the diameter of the catheter shaft 102) or non-existent without risking the wrapped catheter shaft 102 disengaging from the introducer cap assembly 110. Decreasing the depth of the groove 120 or eliminating the groove 120 in selected locations may be advantageous in that less material is required to form the introducer cap assembly 110 (because the faces 122 and 124 may be smaller overall), thereby decreasing the cost of the catheter assembly 100 and increasing the speed at which the introducer cap assembly 110 deteriorates or dissolves in water. Additionally, the extensions 126, if provided, may serve as gripping surfaces or elements for a user during use of the catheter assembly 100 for improved handling and manipulation. While extensions 126 may provide several advantages, it is also within the scope of the present disclosure for the introducer cap assembly 110a of a catheter assembly 100a to be provided without extensions, as in the embodiment of FIGS. 13 and 14.

In addition to extensions 126, one or both of the lateral portions 114 and 116 may additionally or alternatively include one or more holes 128, as shown in the embodiment of FIG. 10. The hole 128 may pass through the introducer cap assembly 110b from the front face 122 to the rear face 124, which increases the surface area of the introducer cap assembly 110b. This may be advantageous by increasing the amount of surface area contacted by moving water when the catheter assembly 100 is flushed down a toilet, which may assist in moving the catheter assembly 100 through a wastewater drainage pipe. Additionally, exposing more surface area to water will increase the speed at which the introducer cap assembly 110b deteriorates or dissolves in water. In the illustrated embodiment, one of the lateral portions 114 (i.e., the smaller lateral portion) includes only one hole 128, with the lateral portion 114 being only large enough to provide a border for the hole 128. As for the other lateral portion 116, it is illustrated with four holes 128 arranged in a generally circular pattern, rather than being positioned adjacent to the associated extensions 126, although it is also within the scope of the present disclosure for one or more extension 126 to have a hole 128 associate therewith. It should be understood that the illustrated configuration is merely exemplary, and it is within the scope of the present disclosure for the introducer cap assembly 110b to include fewer or more holes 128 than the number illustrated and/or for the holes 128 to be differently shaped, arranged, and oriented.

Figure 11:
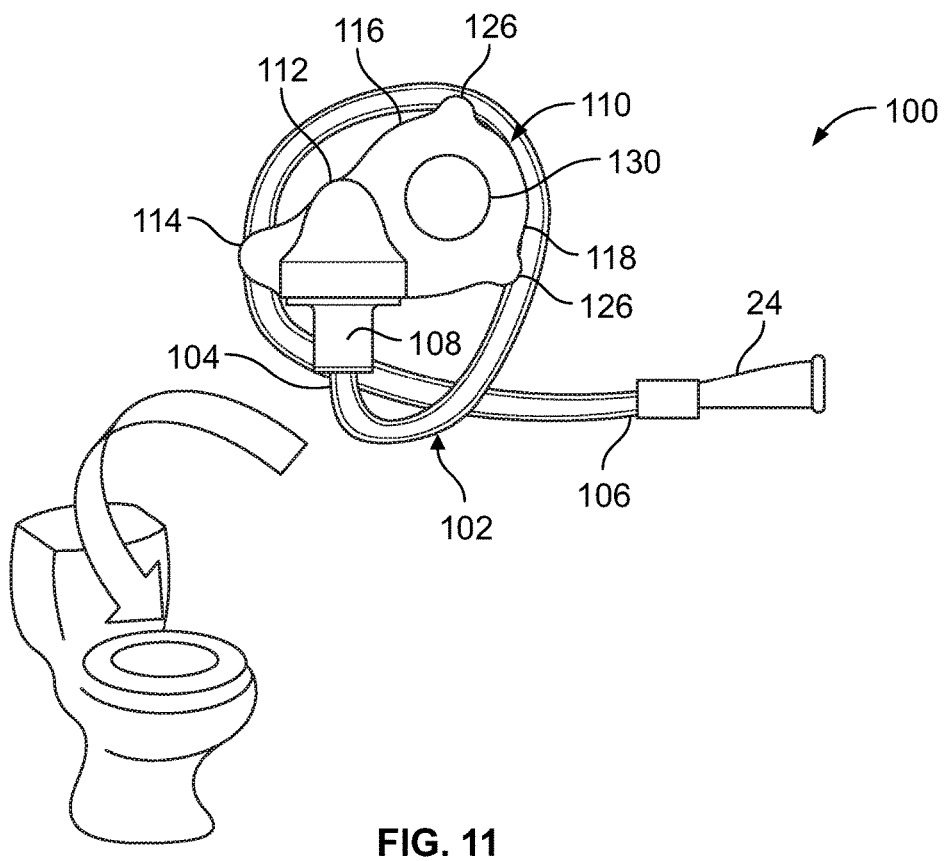
FIG. 11 is a front elevational view of a catheter shaft wrapped around the cap assembly of FIG. 8.
Figure 12:
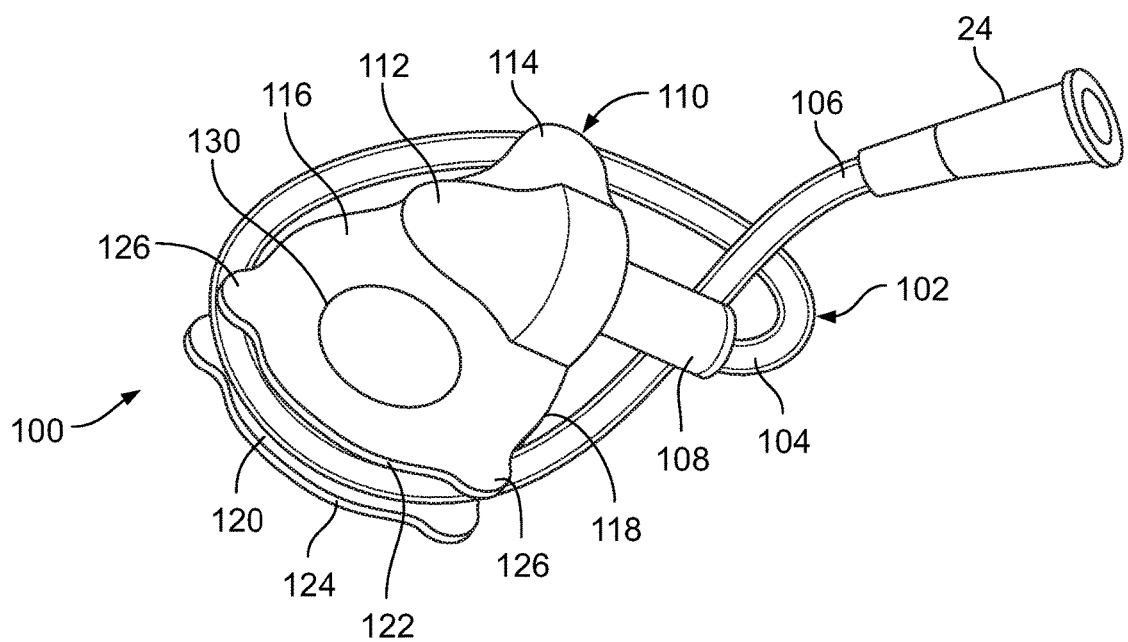
FIG. 12 is a perspective view of the catheter shaft and cap assembly of FIG. 11.
Figure 13:
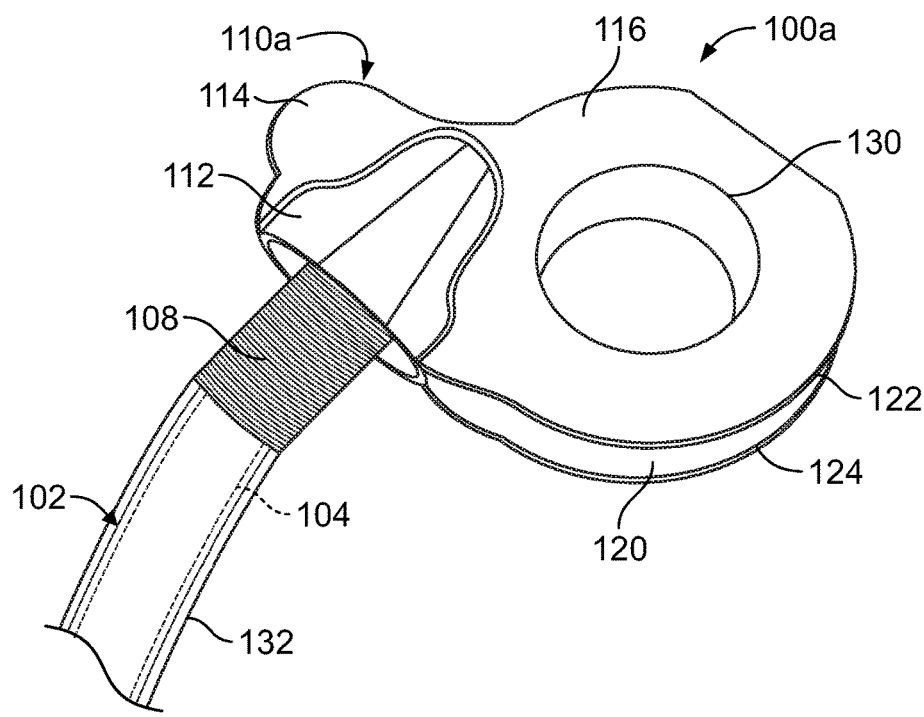
FIG. 13 is a perspective view of an alternative embodiment of a cap assembly of a urinary catheter according to an aspect of the present disclosure.

Similar to the funnel assemblies of FIGS. 1-7, introducer cap assemblies according to the present disclosure may define an opening 130 sized and oriented to receive at least one digit or finger of a user. If provided, the opening 130 allows for improved handling, as described above in greater detail, while also allowing for a more secure attachment of the catheter shaft 102 to the introducer cap assembly after use. In particular, the catheter shaft 102 may be wrapped around the introducer cap assembly, with a portion of the catheter shaft 102 positioned within the groove 120 to define an at least partial loop. The distal end portion 106 may then be passed through the loop via the opening 130 in the introducer cap assembly to effectively tie the catheter shaft 102 in a simple knot, which retains the catheter shaft 102 on the introducer cap assembly in a compact orientation (FIGS. 11 and 12). The compact orientation decreases the footprint and compacts the mass of the catheter assembly, which may improve movement of the catheter assembly through a wastewater drainage pipe when flushed down a toilet.

Turning now to an exemplary method of using the catheter assembly 100 for draining the bladder of a male, it is first removed from a package, if provided. If the catheter shaft 102 is not formed of an inherently lubricious material or provided with a lubricious coating, it may be preferred to apply a lubricant to the outer surface of the catheter shaft 102 for improved comfort as the user advances the catheter shaft 102 through the urethra to the bladder. The catheter shaft 102 may be housed within a protective sleeve 132, as in the embodiment of FIGS. 13 and 14, to shield it from the outside environment prior to advancement into the urethra or it may be uncovered, as in FIGS. 8-12. As described above in greater detail, it may be advantageous to include a protective sleeve 132 for post-use handling of the catheter shaft 102.

When free of the package, the introducer cap assembly 110 is removed from the introducer tip 108, and then a proximal portion of the introducer tip 108 is advanced into the urethra. With the introducer tip 108 partially positioned within the urethra, the catheter shaft 102 may be moved proximally with respect to the introducer tip 108 to advance the proximal end portion 104 of the catheter shaft 102 out of the introducer tip 108 and into the urethra without exposing the end of the catheter shaft 102 to the outside environment. When the catheter shaft 102 has been advanced into the urethra to the point that the eyes of the proximal end portion 104 are positioned within the bladder, urine from the bladder will flow into the eyes, through the catheter shaft 102 and to the distal end portion 106 of the catheter shaft 102. The urine exits the catheter assembly 100 via the funnel 24, into a collection container or a disposal device (e.g., a toilet). Thereafter, the user may grip the funnel 24 and move the funnel 24 distally away from the body to withdraw the catheter shaft 102 and introducer tip 108 from the urethra.

Figure 14:
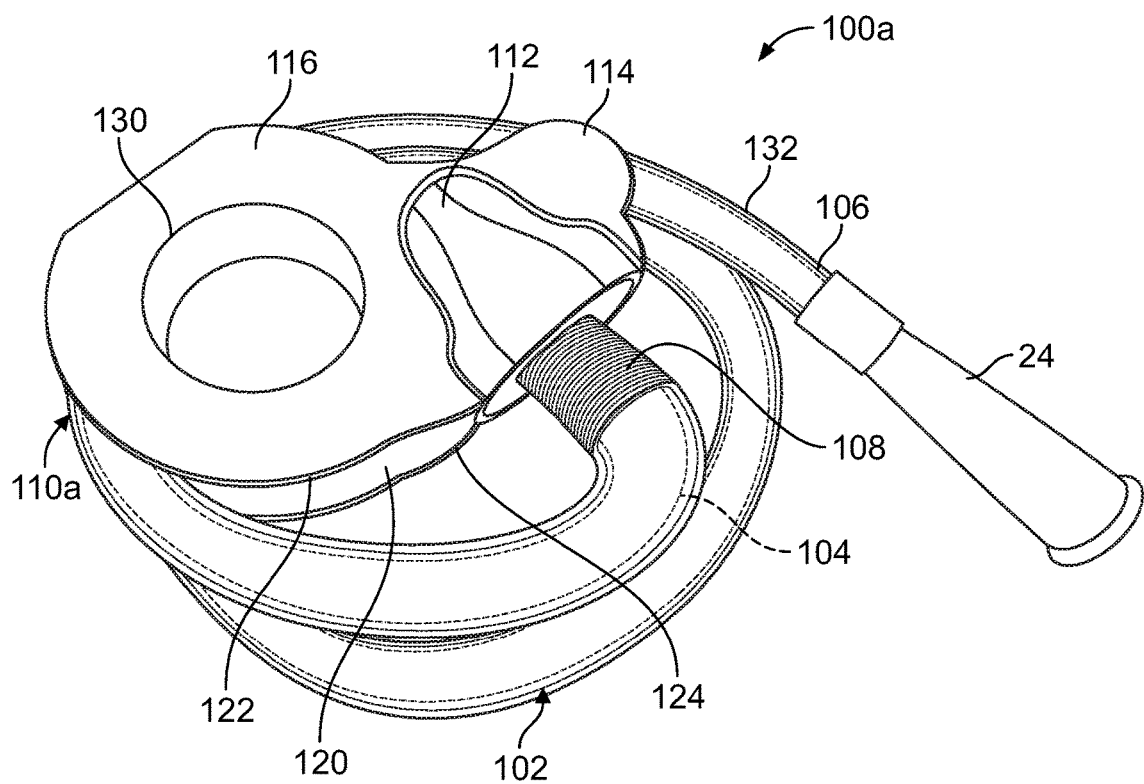
FIG. 14 is a perspective view of a catheter shaft wrapped around the cap assembly of FIG. 13.
Figure 19:
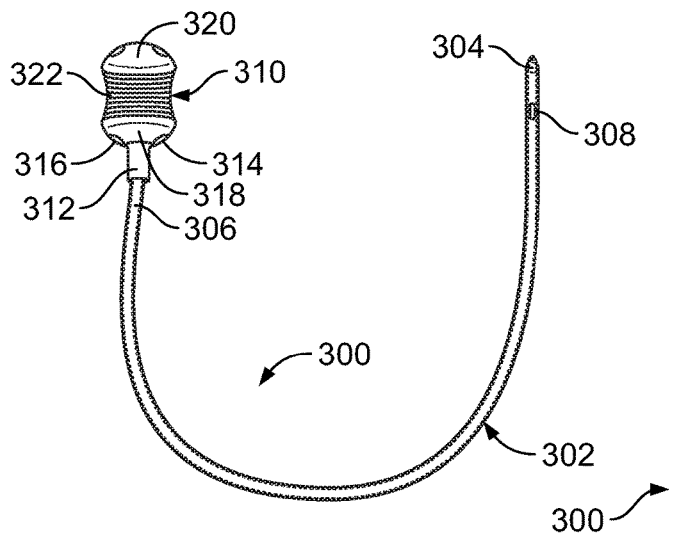
FIG. 19 is a perspective view of another embodiment of a flushable catheter assembly according to an aspect of the present disclosure.
Figure 20:
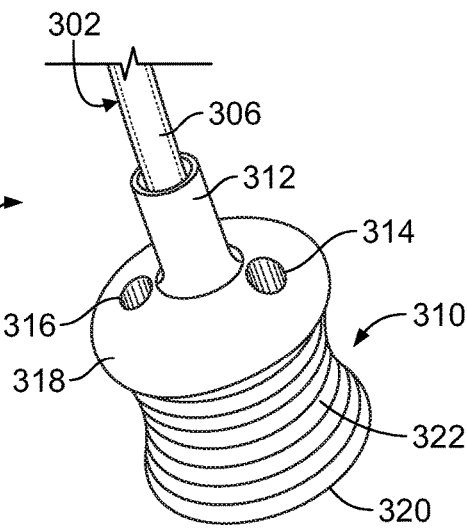
FIG. 20 is a perspective view of the funnel assembly of the catheter assembly of FIG. 19.

Following use, the introducer cap assembly 110 is placed back onto the introducer tip 108 and the catheter shaft 102 may be wrapped around the introducer cap assembly 110 to provide a more compact configuration for disposal (FIGS. 11-12 and 14). If the introducer cap assembly 110 includes an opening 130, the distal end portion 106 of the catheter shaft 102 may be passed through the opening 130 after the catheter shaft 102 has been looped around the introducer cap assembly 110 to effectively tie the catheter shaft 102 in a simple knot to retain the catheter shaft 102 in the compact, wrapped or looped or coiled orientation (FIGS. 11 and 12).

With the catheter assembly 100 in a compact configuration, it may be disposed of by any suitable means, preferably by being flushed down a toilet, with the compact configuration aiding passage of the catheter assembly 100 through the sewage system. As described above, the catheter shaft 102 may be formed of a water disintegrable material to cause it to break down as it passes through the sewage system. The introducer cap assembly 110 is preferably formed of a water disintegrable material and/or an activation agent material configured to aid in the breakdown of the catheter assembly 100 in water. By way of example, the combination of sodium bicarbonate (incorporated into the catheter shaft 102 or the introducer cap assembly 110) and acetic acid (incorporated into the other one of the catheter shaft 102 or the introducer cap assembly 110) in water creates a bubbling effect which increases the speed at which the catheter assembly 100 will break down after being placed into a toilet and flushed.

FIGS. 15-18 show another embodiment of a catheter assembly 200 according to an aspect of the present disclosure. The catheter assembly 200 includes an elongated catheter shaft 202 having a proximal end portion 204 (FIGS. 17 and 18) and a distal end portion 206. The proximal end portion 204 of the catheter shaft 202 is suitable for insertion into a lumen or a passageway of the body, such as the urethra. The proximal end portion 204 may include one or more draining holes or eyes 208 for the drainage of bodily fluids therethrough and into an internal conduit or lumen of the catheter shaft 202.

Fluid entering the catheter shaft 202 via the eye 208 flows from the proximal end portion 204 to the distal end portion 206. The distal end portion 206 may include an associated drainage member or funnel assembly 210 for fluidly connecting the flow path defined by the catheter shaft 202 to a collection container, such as a collection bag, or for directing urine into a waste container, such as a toilet. As described above with respect to the catheter assemblies of FIGS. 1-14, the catheter assembly 200 of FIGS. 15-18 and/or its component parts may be water disintegrable, being formed of one or more materials that are configured to structurally break down when contacted by water (e.g., water in a toilet and associated sewer system).

The funnel assembly 210 includes a generally tubular drainage portion 212, which communicates with and is configured to drain fluid from the catheter shaft 202. On account of having a generally tubular, rather than a generally conical drainage portion 212, the funnel assembly 210 of FIGS. 15-18 may be smaller than the funnel assemblies 20, 20a, and 20b of FIGS. 1-7. This may be advantageous when disposing of the catheter assembly 200 by flushing it down the toilet, as it may be more adept at navigating the tortuous path of the sewer system and there may be less material to be broken down in the water.

The drainage portion 212 may be positioned between a pair of front and rear faces 214 and 216, which may be wider than the drainage portion 212 in a leteral direction to define an outer perimeter 218 of the funnel assembly 210. The relatively wide front and rear faces 214 and 216 define therebetween a groove 220 on each lateral side of the drainage portion 212. In the illustrated embodiment, the front and rear faces 214 and 216 are substantially parallel at least in the vicinity of the grooves 220, such that the grooves 220 are defined between substantially parallel surfaces. The grooves 220 are preferably configured to receive at least a portion of the catheter shaft 202 when the catheter shaft 202 is wrapped around the funnel assembly 210 (FIGS. 16-18). Accordingly, the width of each groove 220 (i.e., the distance between the faces 214 and 216) is preferably at least as great as the diameter of the catheter shaft 202, to allow the catheter shaft 202 to be received within the grooves 220. Alternatively, a portion of each groove 220 (e.g., an outermost portion) may be less than the diameter of the catheter shaft 202, in which case the resiliently deformable catheter shaft 202 may be temporarily deformed and pressed into the grooves 220 to better retain the catheter shaft 202 in a wrapped orientation around the funnel assembly 210.

The depth of each groove 220 (i.e., the dimension in the lateral direction) may be either substantially uniform or vary along the outer perimeter 218 of the funnel assembly 210. In the illustrated embodiment, the front and rear faces 214 and 216 are substantially identical, with each having a generally convex deltoid shape (similar to a kite or an arrowhead or a shield or a strawberry), which results in grooves 220 having a varying depth along the length of the funnel assembly 210. The illustrated faces 214 and 216 are wider in a proximal section 222 than in a distal section 224, resulting in grooves 220 having a varying depth that decreases in the distal direction. Such a configuration provides sufficient depth at selected (i.e., more proximal) locations to retain the catheter shaft 202, while decreasing the total amount of material required to form the funnel assembly 210. The illustrated faces 214 and 216 also have tapered thicknesses, resulting in a funnel assembly 210 having a thickness (i.e., the dimension in the vertical direction in the orientation of FIG. 15) that decreases in the distal direction. Such a configuration may improve the handling of the funnel assembly 210 by a user, as it provides contoured surfaces that a user may grip or pinch when inserting or retracting the catheter shaft 202 from a body lumen.

Following use (as described above in greater detail with respect to the embodiments of FIGS. 1-14), the catheter shaft 202 may be wrapped around the funnel assembly 210 to provide a more compact configuration for disposal (FIGS. 16-18). In the illustrated embodiment, the catheter shaft 202 (which may be at least partially positioned within a protective sleeve) is moved toward the funnel assembly 210 and pressed or otherwise positioned into one of the grooves 220 (FIG. 16). The catheter shaft 202 is then curled around the distal portion 224 of the funnel assembly 210 and pressed or otherwise positioned into the other groove 220 (FIG. 17). The proximal end portion 204 of the catheter shaft 202 may be advanced through a loop 226 defined by the distal portion of the catheter shaft 202 and then pulled tighter to reduce the size of the loop 226 and effectively tie the catheter shaft 202 in a simple knot to retain the catheter shaft 202 in a compact, wrapped or looped or coiled orientation (FIG. 18) around the funnel assembly 210.

With the catheter assembly 200 in a compact configuration, it may be disposed of by any suitable means. Most notably, the catheter assembly 200 may be flushed down a toilet, with the compact configuration aiding passage of the catheter assembly 200 through the sewage system. The tapered, "arrowhead" or pyramidal configuration of the funnel assembly 210 may help to orient the catheter assembly 200 as it traverses the sewage system, with the aerodynamic funnel assembly 210 leading the loop 226 of the catheter shaft 202 as the catheter assembly 200 moves through the sewage system. As described above, the catheter shaft 202 and other components of the catheter assembly 200 may be formed of a water disintegrable material to cause the catheter assembly 200 to break down as it passes through the sewage system.

FIGS. 19-24 show another embodiment of a catheter assembly 300 according to an aspect of the present disclosure. The catheter assembly 300 includes an elongated catheter shaft 302 having a proximal end portion 304 and a distal end portion 306. The proximal end portion 304 of the catheter shaft 302 is suitable for insertion into a lumen or a passageway of the body, such as the urethra. The proximal end portion 304 may include one or more draining holes or eyes 308 for the drainage of bodily fluids therethrough and into an internal conduit or lumen of the catheter shaft 302.

Fluid entering the catheter shaft 302 via the eye 308 flows from the proximal end portion 304 to the distal end portion 306. The distal end portion 306 may include an associated drainage member or funnel assembly 310 for fluidly connecting the flow path defined by the catheter shaft 302 to a collection container, such as a collection bag, or for directing urine into a waste container, such as a toilet. As described above with respect to the catheter assemblies of FIGS. 1-18, the catheter assembly 300 of FIGS. 19-24 and/or its component parts may be water disintegrable, being formed of one or more materials that are configured to structurally break down when contacted by water (e.g., water in a toilet and associated sewer system).

The funnel assembly 310 (which may be formed of one or more of the materials listed above) includes a generally tubular drainage portion 312, which communicates with and is configured to drain fluid from the catheter shaft 302. In addition to defining a first hollow passage (i.e., the drainage portion 312), the body of the funnel assembly 310 defines two additional hollow passages, which are referred to herein as shaft channels 314 and 316. In the illustrated embodiment, the body of the funnel assembly 310 is generally cylindrical, with the shaft channels 314 and 316 being positioned on opposite sides of the drainage portion 312, but the funnel assembly 310 may be differently shaped and/or the shaft channels 314 and 316 may be differently positioned (e.g., spaced apart at a non-180° angle) without departing from the scope of the present disclosure. The outer surface of the body of the funnel assembly 310 surrounding the drainage portion 312 and the shaft channels 314 and 316 may be contoured for improved grip and handling, such as in the illustrated embodiment, which is generally spool-shaped, with enlarged proximal and distal ends 318 and 320 separated by a concave midsection 322 that may be gripped by a user.

Figure 21:
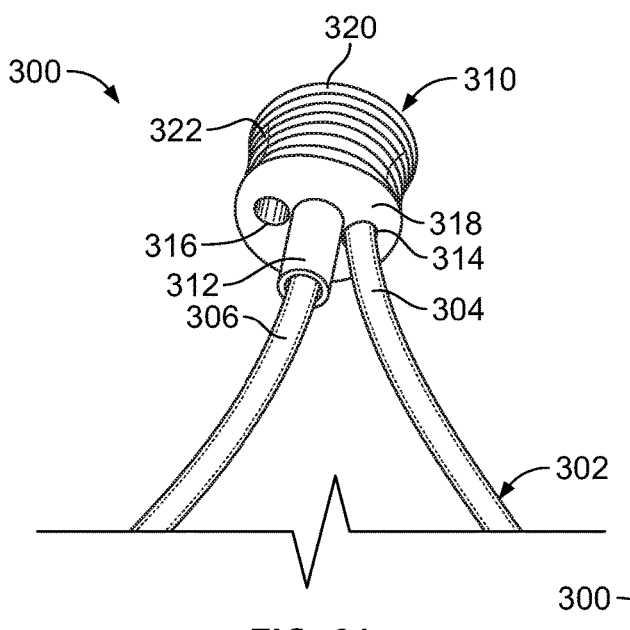
FIG. 21 is a perspective view of the funnel assembly of FIG. 20, with a catheter shaft partially positioned therein.
Figure 22:
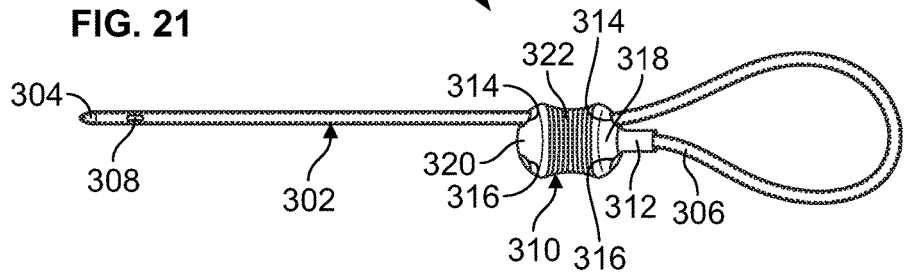
FIGS. 22 and 23 are front elevational views of the funnel assembly of FIG. 20, with a catheter shaft partially looped therethrough.
Figure 23:
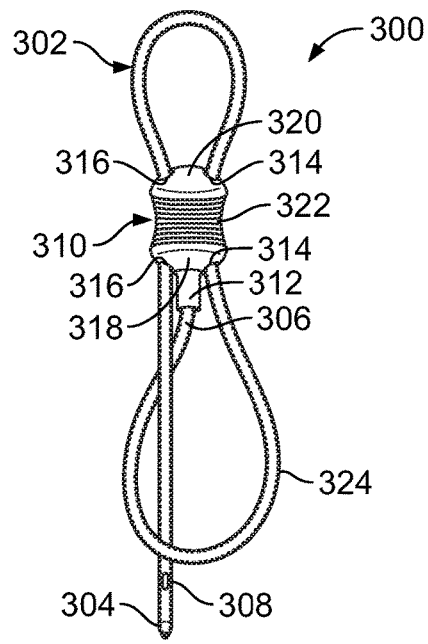
Figure 24:
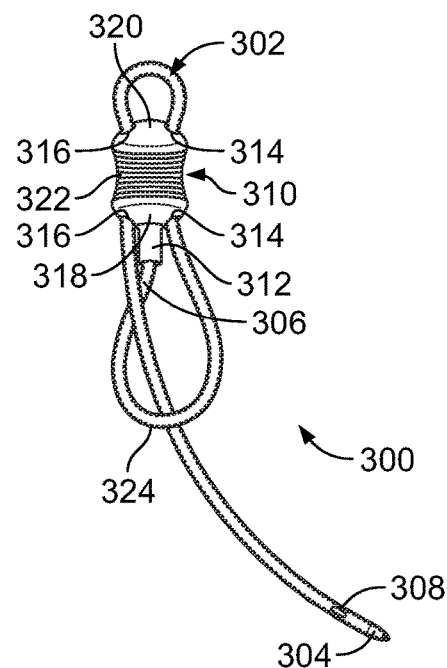
FIG. 24 is a front elevational view of the funnel assembly of FIG. 20, with a catheter shaft fully looped therethrough for improved disposability.

The shaft channels 314 and 316 are configured to receive the catheter shaft 302 for disposal of the catheter assembly 300 after use. FIGS. 21 and 22 illustrate the catheter shaft 302 being curled toward the funnel assembly 310 to press or otherwise advance the proximal end portion 304 into an opening of one of the shaft channels 314. The proximal end portion 304 of the catheter shaft 302 is then advanced through the shaft channel 314 from the proximal end 318 of the funnel assembly 310 to the distal end 320, where the proximal end portion 304 exits the shaft channel 314, with a more distal portion of the catheter shaft 302 remaining in the shaft channel 314. The portion of the catheter shaft 302 extending from the distal end 320 of the funnel assembly 310 is then curled back toward the funnel assembly 310 to press or otherwise advance the proximal end portion 304 into an opening of the other shaft channel 316 at the distal end 320 of the funnel assembly 310 (FIG. 23). The proximal end portion 304 of the catheter shaft 302 is then advanced through this shaft channel 316 from the distal end 320 of the funnel assembly 310 to the proximal end 318, where the proximal end portion 304 exits the second shaft channel 316 via an opening at the proximal end 318 of the funnel assembly 310. The proximal end portion 304 of the catheter shaft 302 may then be advanced through a loop 324 defined by the portion of the catheter shaft 302 extending between the drainage portion 312 of the funnel assembly 310 (i.e., the distal end portion 306 of the catheter shaft 302) and the opening of the first shaft channel 314 at the proximal end 318 of the funnel assembly 310 to decrease or minimize the portion of the catheter shaft 302 protruding from the distal end 320 of the funnel assembly 310. Passing the proximal end portion 304 of the catheter shaft 302 also serves to effectively tie the catheter shaft 302 in a simple knot to retain the catheter shaft 302 in a compact, wrapped or looped or coiled orientation (FIG. 24) within the funnel assembly 310.

With the catheter assembly 300 in a compact configuration, it may be disposed of by any suitable means. Most notably, the catheter assembly 300 may be flushed down a toilet, with the compact configuration aiding passage of the catheter assembly 300 through the sewage system. The denser, heavier funnel assembly 310 may help to orient the catheter assembly 300 as it traverses the sewage system, with the funnel assembly 310 leading the loop 324 of the catheter shaft 302 as the catheter assembly 300 moves through the sewage system. As described above, the catheter shaft 302 and other components of the catheter assembly 300 may be formed of a water disintegrable material to cause the catheter assembly 300 to break down as it passes through the sewage system.

The shaft channels 314 and 316 may be variously configured without departing from the scope of the present disclosure. Between the access openings at the proximal and distal ends 318 and 320 of the funnel assembly 310, the shaft channels 314 and 316 may be generally linear (e.g., parallel to the drainage portion 312) or curved (e.g., with a curvature that matches the curvature of the outer surface of the funnel assembly 310 or a different curvature). The two shaft channels 314 and 316 may be identical or differently configured. It may be advantageous for the shaft channels 314 and 316 to be configured to assist in threading the catheter shaft 302 through the funnel assembly 310. For example, the opening of the first shaft channel 314 at the distal end 320 of the funnel assembly 310 may be angled toward the opening of the second shaft channel 316 at the distal end 320 of the funnel assembly 310 to direct the proximal end portion 304 of the catheter shaft 302 toward the second shaft channel 316 as it exits the first shaft channel 314, to be passed back through the second shaft channel 316. Similarly, the opening of the second shaft channel 316 at the proximal end 318 of the funnel assembly 310 may be angled toward the opening of the first shaft channel 314 at the proximal end 318 of the funnel assembly 310 to direct the proximal end portion 304 of the catheter shaft 302 through the loop 324 of the catheter shaft 302 as it exits the second shaft channel 316. Additionally, it may be advantageous for one or more of the openings of the shaft channels 314 and 316 to have a larger diameter than the portions of the shaft channels 314 and 316 defined within the midsection 322 of the funnel assembly 310 to facilitate alignment of the proximal end portion 304 of the catheter shaft 302 and the opening.

Figure 25:
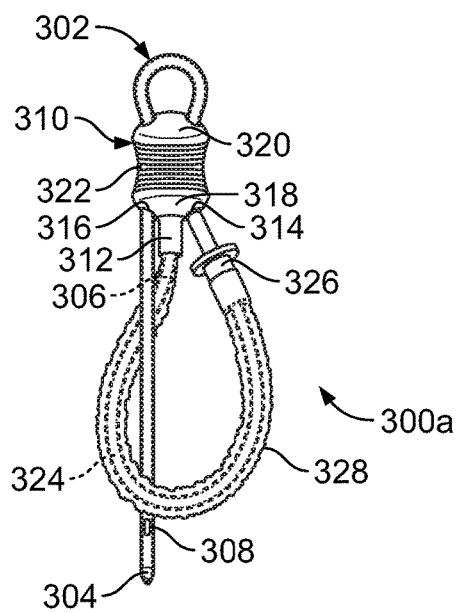
FIG. 25 is a perspective view of a variation of the flushable catheter assembly of FIG. 19.

FIG. 25 illustrates a catheter assembly 300a that is a variation of the catheter assembly 300 of FIGS. 19-24. The catheter assembly 300a of FIG. 25 is identical to the catheter assembly 300 of FIGS. 19-24, except it further includes an introducer tip 326, with a protective sleeve 328 extending between the introducer tip 326 and the funnel assembly 310 to enclose the catheter shaft 302. The introducer tip 326 may be larger than the openings of the shaft channels 314 and 316, in which case the introducer tip 326 may be positioned against the opening of one of the shaft channels 314 at the proximal end 318 of the funnel assembly 310, with the proximal end portion 304 of the catheter shaft 302 being advanced out of the proximal end of the introducer tip 326 to enter the shaft channel 314. Thereafter, the catheter shaft 302 may be manipulated to secure it through and within the funnel assembly 310 as described above with respect to the embodiment of FIGS. 19-24.

Figure 26:
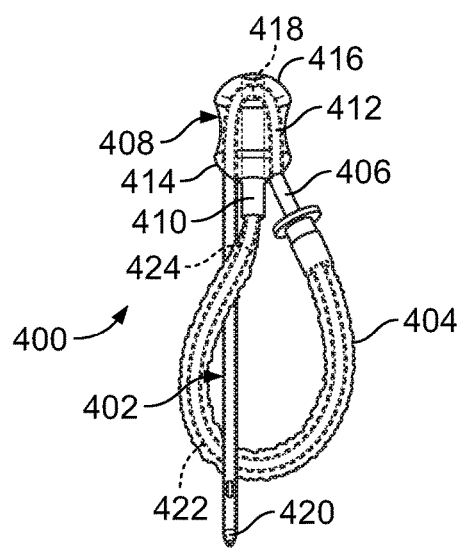
FIG. 26 is a perspective view of another variation of the flushable catheter assembly of FIG.

FIG. 26 illustrates a catheter assembly 400 that is a variation of the catheter assembly 300a of FIG. 25. As in the embodiment of FIG. 25, the catheter assembly 400 of FIG. 26 includes a catheter shaft 402 positioned within a protective sleeve 404 that extends between an introducer tip 406 at its proximal end and a funnel assembly 408 at its distal end. The funnel assembly 408 may be shaped similarly to the funnel assemblies 310 of FIGS. 19-25, with a centrally located drainage portion 410 that is in fluid communication with the catheter shaft 402 for draining fluid from the catheter shaft 402, or it may be differently shaped.

As in the embodiments of FIGS. 19-25, a shaft channel 412 is defined within the body of the funnel assembly 408, but rather than providing two shaft channels with openings at the proximal and distal ends 414 and 416 of the funnel assembly 408, the shaft channel 412 of FIG. 26 includes only two openings at the proximal end 414 of the funnel assembly 408. The illustrated shaft channel 412 is generally U-shaped, and extends from one of the openings toward the distal end 416 of the funnel assembly 408. Before reaching the distal end 416 of the funnel assembly 408, the shaft channel 412 turns toward the central axis of the funnel assembly 408 and passes through the drainage portion 410 to the other side of the body of the funnel assembly 408, where it bends back toward the proximal end 414 of the funnel assembly 408 and extends to the other opening. In one embodiment, the shaft channel 412 includes a generally tubular bridge 418 that passes through the drainage portion 410 to connect the two sections of the shaft channel 412. If provided, such a bridge 418 preferably has a diameter that is less than the diameter of the drainage portion 410 to allow fluid to flow through the drainage portion 410 without being blocked by the bridge 418.

After use of the catheter assembly 400 (in accordance with the foregoing description of the method of using the other catheter assemblies), the catheter shaft 402 may be curled toward the funnel assembly 408 to press the introducer tip 406 against one of the openings of the shaft channel 412. The proximal end portion 420 of the catheter shaft 402 may then be advanced out of the introducer tip 406 and into the shaft channel 412. The proximal end portion 420 of the catheter shaft 402 is then advanced through the entire shaft channel 412 until it exits the other opening of the shaft channel 412, with a more distal portion of the catheter shaft 402 remaining in the shaft channel 412. The proximal end portion 420 of the catheter shaft 402 may then be advanced through a loop 422 defined by the portion of the catheter shaft 402 extending between the drainage portion 410 of the funnel assembly 410 (i.e., the distal end portion 424 of the catheter shaft 402) and the introducer tip 406 to effectively tie the catheter shaft 402 in a simple knot to retain the catheter shaft 402 in a compact, wrapped or looped or coiled orientation within the funnel assembly 408.

With the catheter assembly 400 in a compact configuration, it may be disposed of by any suitable means. Most notably, the catheter assembly 400 may be flushed down a toilet, with the compact configuration aiding passage of the catheter assembly 400 through the sewage system. The denser, heavier funnel assembly 408 may help to orient the catheter assembly 400 as it traverses the sewage system, with the funnel assembly 408 leading the loop 422 of the catheter shaft 402 as the catheter assembly 400 moves through the sewage system. As described above, the catheter assembly 400 and/or its component parts may be formed of a water disintegrable material to cause the catheter assembly 400 to break down as it passes through the sewage system.

It may be advantageous for the one or more of the various components of the catheter assemblies described herein (namely, the catheter shaft, funnel, and/or introducer cap assembly) to have a selected density for improving the flow of the catheter assembly through the pipes of a sewage system. For example, it may be preferred for the catheter assembly and/or its individual components (including the catheter shaft, funnel, and introducer cap assembly) to have a density in the range of approximately 0.40 g/cm$^3$ to approximately 1.20 g/cm$^3$, although it is also within the scope of the present disclosure for the catheter assembly or one or more of its individual components to have a density that is outside of this range. More preferably, the catheter shaft, funnel, and/or introducer cap assembly may have a density in the range of approximately 0.68 g/cm$^3$ to approximately 0.89 g/cm$^3$. Such densities may be advantageous in causing the catheter assembly in the compact configuration to assume a particular orientation and/or to rest at a particular depth in water or to otherwise self-orient in an advantageous direction to facilitate flushing and disposal, but it is within the scope of the present disclosure for the catheter shaft, funnel, and/or introducer cap assembly to have a different density and/or for different portions of the catheter shaft, funnel, and/or introducer cap assembly to have different densities and/or buoyancies.

Figure 27:
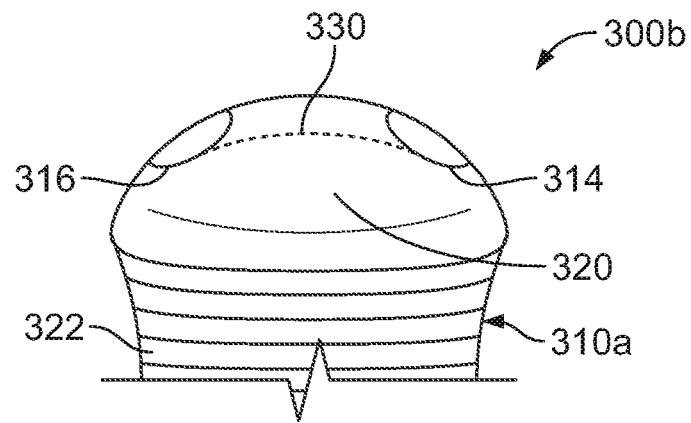
FIG. 27 is a front elevational view of a variation of the flushable catheter assembly of FIG. 19.
Figure 28:
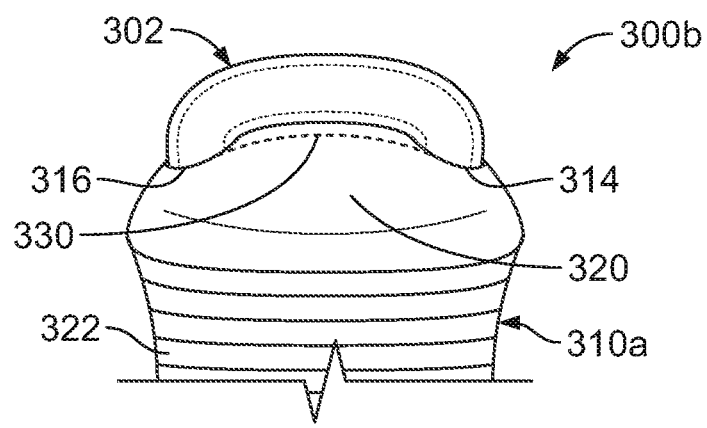
FIG. 28 is a front elevational view of the flushable catheter assembly of FIG. 27, with a catheter shaft fully looped therethrough for improved disposability.

It should be understood that the methods described herein are merely exemplary, and that the steps described above may be carried out in a different order. Further, other steps may be included when using the devices described herein. Additionally, one or more of the steps described herein in connection with the methods may be omitted or modified without departing from the scope of the present disclosure. Similarly, the devices described herein are merely exemplary, and they may be differently configured (e.g., by combining one or more components of one described embodiment with one or more components of another described embodiment) without departing from the scope of the present disclosure. For example, the funnel assemblies 310 and 408 may be provided with one or more openings to receive the digit of a user or a portion of a catheter shaft and/or one or more holes to trap water, or a single funnel assembly may include both a perimeter groove and a shaft channel to receive separate portions of a catheter shaft. FIGS. 27 and 28 show such catheter assembly 300b, with a funnel assembly 310a configured as in FIGS. 19-24, but including a perimeter groove 330. The catheter shaft 302 is wrapped around the funnel assembly 310a as described above with respect to the embodiment of FIGS. 19-24, though the groove 330 allows for the catheter shaft 302 to be more closely wrapped around the funnel assembly 310a, rather than forming a loop (as in FIG. 24).

Aspects of the present subject matter described above may be beneficial alone or in combination with one or more other aspects. Without limiting the foregoing description, in accordance with one aspect of the subject matter herein, there is provided a catheter assembly, which includes a catheter shaft having proximal and distal end portions. A funnel assembly is associated with the distal end portion of the catheter shaft, with a drainage portion being defined through the funnel assembly. The funnel assembly includes a groove along at least a portion of its outer perimeter or a shaft channel defined through the funnel assembly. The groove and/or shaft channel is configured to receive at least a portion of the catheter shaft for securing the catheter shaft to the funnel assembly for disposal.

In accordance with another aspect which may be used or combined with the first aspect, the shaft channel extends between a proximal shaft channel opening associated with a proximal end of the funnel assembly and a distal shaft channel opening associated with a distal end of the funnel assembly.

In accordance with another aspect which may be used or combined with the preceding aspect, a second shaft channel is defined through the funnel assembly and extends between a proximal second shaft channel opening associated with the proximal end of the funnel assembly and a distal second shaft channel opening associated with the distal end of the funnel assembly.

In accordance with another aspect which may be used or combined with the first aspect, the shaft channel extends between first and second proximal shaft channel openings associated with a proximal end of the funnel assembly.

In accordance with another aspect which may be used or combined with any of the preceding aspects, the funnel assembly defines an opening, which is configured to receive at least one digit of a user or a portion of the catheter shaft.

In accordance with another aspect which may be used or combined with any of the preceding aspects, the funnel assembly defines at least one hole configured to trap water and improve movement of the catheter assembly through a drainage pipe.

In accordance with another aspect which may be used or combined with any of the preceding aspects, the catheter shaft and/or the funnel assembly is at least partially comprised of a water disintegrable material.

In accordance with another aspect which may be used or combined with any of the preceding aspects, the funnel assembly is at least partially comprised of an activation agent material configured to aid in the breakdown of the catheter shaft and/or the funnel assembly in water.

In accordance with another aspect which may be used or combined with any of the preceding aspects, at least a portion of the catheter shaft is formed of a material including sodium bicarbonate and at least a portion of the funnel assembly is formed of a material including acetic acid.

In accordance with another aspect which may be used or combined with any of the first through eighth aspects, at least a portion of the funnel assembly is formed of a material including sodium bicarbonate and at least a portion of the catheter shaft is formed of a material including acetic acid.

In accordance with another aspect, there is provided a catheter assembly, which includes a catheter shaft having proximal and distal end portions. An introducer tip is associated with the proximal end portion of the catheter shaft, with an introducer cap assembly removably connected to the introducer tip. A groove is defined along at least a portion of the outer perimeter of the introducer cap assembly, with the groove being configured to receive at least a portion of the catheter shaft for wrapping the catheter shaft around the outer perimeter of the introducer cap assembly.

In accordance with another aspect which may be used or combined with the preceding aspect, the introducer cap assembly defines an opening configured to receive at least one digit of a user or a portion of the catheter shaft.

In accordance with another aspect which may be used or combined with any of the preceding two aspects, the catheter shaft and/or the introducer cap assembly is at least partially comprised of a water disintegrable material.

In accordance with another aspect which may be used or combined with any of the preceding three aspects, the introducer cap assembly is at least partially comprised of an activation agent material configured to aid in the breakdown of the catheter shaft and/or the introducer cap assembly in water.

In accordance with another aspect which may be used or combined with any of the preceding four aspects, at least a portion of the catheter shaft is formed of a material including sodium bicarbonate and at least a portion of the introducer cap assembly is formed of a material including acetic acid.

In accordance with another aspect which may be used or combined with any of the eleventh through fourteenth aspects, at least a portion of the introducer cap assembly is formed of a material including sodium bicarbonate and at least a portion of the catheter shaft is formed of a material including acetic acid.

In accordance with another aspect which may be used or combined with any of the preceding six aspects, the introducer cap assembly defines at least one hole configured to trap water and improve movement of the catheter assembly through a drainage pipe.

In accordance with another aspect, there is provided a method of disposing of a catheter assembly of the type having a catheter shaft and a funnel assembly associated with a distal end portion of the catheter shaft. The method includes securing at least a portion of the catheter shaft to the funnel assembly by wrapping the catheter shaft around an outer perimeter of the funnel assembly so as to position at least a portion of the catheter shaft within a groove defined along at least a portion of the perimeter. Alternatively (or additionally) at least a portion of the catheter shaft may be passed through a shaft channel defined through the funnel assembly to secure the catheter shaft to the funnel assembly prior to placing the catheter assembly in a waste container.

In accordance with another aspect which may be used or combined with the preceding aspect, a proximal end portion of the catheter shaft is inserted into the shaft channel at a proximal end of the funnel assembly and advanced through the shaft channel until the proximal end portion of the catheter shaft exits the shaft channel at a distal end of the funnel assembly.

In accordance with another aspect which may be used or combined with the eighteenth aspect, a proximal end portion of the catheter shaft is inserted into the shaft channel at a proximal end of the funnel assembly and advanced through the shaft channel until the proximal end portion of the catheter shaft exits the shaft channel at a distal end of the funnel assembly. The proximal end portion of the catheter shaft may then be passed through the funnel assembly from the distal end of the funnel assembly to the proximal end of the funnel assembly via a second shaft channel defined through the funnel assembly.

In accordance with another aspect which may be used or combined with the eighteenth aspect, a proximal end portion of the catheter shaft is inserted into the shaft channel at a proximal end of the funnel assembly and advanced through the shaft channel until the proximal end portion of the catheter shaft exits the shaft channel at a different portion of the proximal end of the funnel assembly.

In accordance with another aspect which may be used or combined with any of the preceding four aspects, a proximal end portion of the catheter shaft is inserted through an opening defined in the funnel assembly after securing at least a portion of the catheter shaft to the funnel assembly and before placing the catheter assembly in a waste container.

In accordance with another aspect which may be used or combined with any of the preceding five aspects, the catheter assembly is placed in a toilet and flushed the catheter assembly down the toilet.

In accordance with another aspect, there is provided a method of disposing of a catheter assembly of the type having a catheter shaft and an introducer cap assembly associated with a proximal end portion of the catheter shaft. The method includes wrapping the catheter shaft around an outer perimeter of the introducer cap assembly so as to position at least a portion of the catheter shaft within a groove defined along at least a portion of the perimeter prior to placing the catheter assembly in a waste container.

In accordance with another aspect which may be used or combined with the preceding aspect, a loop with the catheter shaft is formed and a distal end portion of the catheter shaft is passed through the loop to secure the catheter shaft around the introducer cap assembly.

In accordance with another aspect which may be used or combined with any of the preceding two aspects, the catheter assembly is placed in a toilet and flushed the catheter assembly down the toilet.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A catheter assembly comprising:
  a catheter shaft having proximal and distal end portions; and
  a funnel assembly fixedly secured to the distal end portion of the catheter shaft, wherein
    a drainage portion is defined through the funnel assembly and the funnel assembly includes
      a groove along at least a portion of an outer perimeter of the funnel assembly and/or
      a shaft channel defined through the funnel assembly, with the groove and/or the shaft channel being configured to receive at least a portion of the catheter shaft for securing said at least a portion of the catheter shaft to the funnel assembly for disposal, the drainage portion is positioned between a pair of lateral portions, each lateral portion includes a front face and a rear face, and the groove is defined between the front and rear faces.

2. The catheter assembly of claim 1, wherein the funnel assembly defines an opening, the opening being configured to receive at least one digit of a user or a portion of the catheter shaft.

3. The catheter assembly of claim 1, wherein the funnel assembly defines at least one hole configured to trap water and improve movement of the catheter assembly through a drainage pipe.

4. The catheter assembly of claim 1, wherein the catheter shaft and/or the funnel assembly is at least partially comprised of a water disintegrable material.

5. The catheter assembly of claim 1, wherein the funnel assembly is at least partially comprised of an activation agent material configured to aid in the breakdown of the catheter shaft and/or the funnel assembly in water.

6. The catheter assembly of claim 1, wherein at least a portion of one of the catheter shaft and the funnel assembly is formed of a material including sodium bicarbonate and at least a portion of the other one of the catheter shaft and the funnel assembly is formed of a material including acetic acid.

7. The catheter assembly of claim 1, wherein a width of the groove is at least as great as a diameter of the catheter shaft.

8. The catheter assembly of claim 1, wherein a width of the groove is less than a diameter of the catheter shaft.

9. The catheter assembly of claim 1, wherein a depth of the groove is at least as great as a diameter of the catheter shaft.

10. The catheter assembly of claim 1, wherein a depth of the groove is less than a diameter of the catheter shaft.

11. The catheter assembly of claim 1, wherein the groove has a varying depth.

12. A catheter assembly comprising:
a catheter shaft having proximal and distal end portions; and
a funnel assembly fixedly secured to the distal end portion of the catheter shaft, wherein
a drainage portion is defined through the funnel assembly and the funnel assembly includes
a groove along at least a portion of an outer perimeter of the funnel assembly and/or
a shaft channel defined through the funnel assembly, with the groove and/or the shaft channel being configured to receive at least a portion of the catheter shaft for securing said at least a portion of the catheter shaft to the funnel assembly for disposal, and said shaft channel extends between a proximal shaft channel opening associated with a proximal end of the funnel assembly and a distal shaft channel opening associated with a distal end of the funnel assembly.

13. The catheter assembly of claim 12, further comprising a second shaft channel defined through the funnel assembly and extending between a proximal second shaft channel opening associated with the proximal end of the funnel assembly and a distal second shaft channel opening associated with the distal end of the funnel assembly.

14. The catheter assembly of claim 12, wherein the catheter shaft and/or the funnel assembly is at least partially comprised of a water disintegrable material.

15. The catheter assembly of claim 12, wherein the funnel assembly is at least partially comprised of an activation agent material configured to aid in the breakdown of the catheter shaft and/or the funnel assembly in water.

16. The catheter assembly of claim 12, wherein at least a portion of one of the catheter shaft and the funnel assembly is formed of a material including sodium bicarbonate and at least a portion of the other one of the catheter shaft and the funnel assembly is formed of a material including acetic acid.

17. A catheter assembly comprising:
a catheter shaft having proximal and distal end portions; and
a funnel assembly fixedly secured to the distal end portion of the catheter shaft, wherein
a drainage portion is defined through the funnel assembly and the funnel assembly includes
a groove along at least a portion of an outer perimeter of the funnel assembly and/or
a shaft channel defined through the funnel assembly, with the groove and/or the shaft channel being configured to receive at least a portion of the catheter shaft for securing said at least a portion of the catheter shaft to the funnel assembly for disposal, and the shaft channel extends between first and second proximal shaft channel openings associated with a proximal end of the funnel assembly.

18. The catheter assembly of claim 17, wherein the catheter shaft and/or the funnel assembly is at least partially comprised of a water disintegrable material.

19. The catheter assembly of claim 17, wherein the funnel assembly is at least partially comprised of an activation agent material configured to aid in the breakdown of the catheter shaft and/or the funnel assembly in water.

20. The catheter assembly of claim 17, wherein at least a portion of one of the catheter shaft and the funnel assembly is formed of a material including sodium bicarbonate and at least a portion of the other one of the catheter shaft and the funnel assembly is formed of a material including acetic acid.

* * * * *